(12) United States Patent
Birrell

(10) Patent No.: US 9,724,566 B2
(45) Date of Patent: *Aug. 8, 2017

(54) EXERCISE DEVICE PATH TRACES

(71) Applicant: Precor Incorporated, Woodinville, WA (US)

(72) Inventor: James S. Birrell, Seattle, WA (US)

(73) Assignee: Precor Incorporated, Woodinville, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/691,532

(22) Filed: Apr. 20, 2015

(65) Prior Publication Data

US 2015/0224365 A1 Aug. 13, 2015

Related U.S. Application Data

(63) Continuation of application No. 13/371,014, filed on Feb. 10, 2012, now Pat. No. 9,011,291.

(51) Int. Cl.
| | | |
|---|---|---|
| *A63B 71/00* | (2006.01) | |
| *A63B 21/005* | (2006.01) | |
| *A63B 24/00* | (2006.01) | |
| *A63B 71/06* | (2006.01) | |
| *A63B 22/06* | (2006.01) | |
| *A63B 22/00* | (2006.01) | |
| *G06F 19/00* | (2011.01) | |

(52) U.S. Cl.
CPC ...... *A63B 24/0087* (2013.01); *A63B 22/0017* (2015.10); *A63B 22/0664* (2013.01); *A63B 71/0622* (2013.01); *A63B 22/0056* (2013.01); *A63B 24/00* (2013.01); *A63B 2022/0682* (2013.01); *A63B 2024/009* (2013.01); *A63B 2071/0647* (2013.01); *G06F 19/3481* (2013.01); *Y10S 482/902* (2013.01)

(58) Field of Classification Search
USPC .......................................................... 482/1, 4
See application file for complete search history.

(56) References Cited

U.S. PATENT DOCUMENTS

| | | | |
|---|---|---|---|
| 4,235,437 A | * | 11/1980 | Ruis ................. A63B 21/00178 482/113 |
| 5,067,710 A | | 11/1991 | Watterson et al. |
| 5,383,829 A | | 1/1995 | Miller |
| 5,489,249 A | | 2/1996 | Brewer et al. |
| 5,512,025 A | | 4/1996 | Dalebout et al. |
| 5,588,938 A | | 12/1996 | Schneider et al. |
| 5,685,804 A | | 11/1997 | Whan-Tong et al. |
| 5,788,610 A | | 8/1998 | Eschenbach |
| 5,919,118 A | | 7/1999 | Stearns et al. |
| 6,024,676 A | | 2/2000 | Eschenbach |
| 6,146,313 A | | 11/2000 | Whan-Tong et al. |
| 6,277,054 B1 | | 8/2001 | Kuo |
| 6,361,476 B1 | | 3/2002 | Eschenbach |
| 6,390,953 B1 | | 5/2002 | Maresh et al. |

(Continued)

*Primary Examiner* — Sundhara Ganesan
*Assistant Examiner* — Shila Jalalzadeh Abyan
(74) *Attorney, Agent, or Firm* — Terence P. O'Brien; Todd A. Rathe

(57) ABSTRACT

An apparatus and method concurrently present a plurality of visible tracings or a single continuous visible tracing that overlaps itself, each of the visible tracings being based upon movement taken by a member of an exercise device.

20 Claims, 12 Drawing Sheets

(56) References Cited

U.S. PATENT DOCUMENTS

| | | | |
|---|---|---|---|
| 6,413,190 B1 * | 7/2002 | Wood | A61B 5/1071 463/36 |
| 6,447,424 B1 | 9/2002 | Ashby et al. | |
| 6,461,277 B2 | 10/2002 | Maresh et al. | |
| 6,482,130 B1 | 11/2002 | Pasero et al. | |
| 6,612,969 B2 | 9/2003 | Eschenbach | |
| 6,749,540 B1 | 6/2004 | Pasero et al. | |
| 6,808,472 B1 | 10/2004 | Hickman | |
| 6,840,892 B1 | 1/2005 | Wu | |
| 6,926,646 B1 | 8/2005 | Nguyen | |
| 6,939,271 B1 | 9/2005 | Whan-Tong et al. | |
| 6,991,587 B1 | 1/2006 | Eschenbach | |
| 6,994,657 B1 | 2/2006 | Eschenbach | |
| 7,022,049 B2 | 4/2006 | Ryan et al. | |
| 7,025,711 B2 | 4/2006 | Eschenbach | |
| 7,052,438 B2 | 5/2006 | Eschenbach | |
| 7,083,549 B1 | 8/2006 | Fan | |
| 7,104,929 B1 | 9/2006 | Eschenbach | |
| 7,121,984 B1 | 10/2006 | Hong | |
| 7,132,531 B1 | 11/2006 | Wellings et al. | |
| 7,169,088 B2 | 1/2007 | Rodgers, Jr. | |
| 7,169,089 B2 | 1/2007 | Rodgers, Jr. | |
| 7,172,531 B2 | 2/2007 | Rodgers, Jr. | |
| 7,175,568 B2 | 2/2007 | Eschenbach | |
| 7,179,201 B2 | 2/2007 | Rodgers, Jr. | |
| 7,201,705 B2 | 4/2007 | Rodgers, Jr. | |
| 7,226,392 B2 | 6/2007 | Hong | |
| 7,244,217 B2 | 7/2007 | Rodgers, Jr. | |
| 7,244,218 B1 | 7/2007 | Lin et al. | |
| 7,316,632 B2 | 1/2008 | Rodgers, Jr. | |
| 7,377,881 B2 | 5/2008 | Moon | |
| 7,485,072 B2 | 2/2009 | Chuang et al. | |
| 7,494,447 B2 | 2/2009 | Eschenbach | |
| 7,494,448 B2 | 2/2009 | Eschenbach | |
| 7,497,808 B2 | 3/2009 | Eschenbach | |
| 7,507,184 B2 | 3/2009 | Rodgers, Jr. | |
| 7,507,185 B2 | 3/2009 | Eschenbach | |
| 7,520,839 B2 | 4/2009 | Rodgers, Jr. | |
| 7,530,926 B2 | 5/2009 | Rodgers, Jr. | |
| 7,556,590 B2 | 7/2009 | Watterson et al. | |
| 7,556,591 B2 | 7/2009 | Chuang et al. | |
| 7,604,573 B2 | 10/2009 | Dalebout et al. | |
| 7,632,219 B2 | 12/2009 | Ohrt et al. | |
| 7,641,598 B2 | 1/2010 | Rodgers, Jr. | |
| 7,645,212 B2 | 1/2010 | Ashby et al. | |
| 7,651,446 B1 | 1/2010 | Eschenbach | |
| 7,678,025 B2 | 3/2010 | Rodgers, Jr. | |
| 7,708,668 B2 | 5/2010 | Rodgers, Jr. | |
| 7,708,669 B2 | 5/2010 | Rodgers, Jr. | |
| 7,717,828 B2 | 5/2010 | Simonson et al. | |
| 7,758,469 B2 | 7/2010 | Dyer et al. | |
| 7,789,800 B1 | 9/2010 | Watterson et al. | |
| 7,794,362 B2 | 9/2010 | Miller | |
| 7,811,208 B2 | 10/2010 | Rodgers, Jr. | |
| 7,815,551 B2 | 10/2010 | Merli | |
| 7,828,698 B2 | 11/2010 | Rodgers, Jr. | |
| 7,841,968 B1 | 11/2010 | Eschenbach | |
| 7,874,963 B2 | 1/2011 | Grind | |
| 7,878,947 B1 | 2/2011 | Rodgers, Jr. | |
| 7,887,465 B2 | 2/2011 | Uffelman | |
| 7,922,625 B2 | 4/2011 | Grind | |
| 7,927,252 B1 * | 4/2011 | Jeffrey | A63B 24/0003 434/247 |
| 7,938,754 B2 | 5/2011 | Eschenbach | |
| 7,988,600 B2 | 8/2011 | Rodgers, Jr. | |
| 7,993,247 B1 | 8/2011 | Eschenbach | |
| 8,021,275 B2 | 9/2011 | Rodgers, Jr. | |
| 8,029,415 B2 | 10/2011 | Ashby et al. | |
| 8,029,416 B2 | 10/2011 | Eschenbach | |
| 2,092,351 A1 | 1/2012 | Rodgers, Jr. | |
| 8,562,491 B2 | 10/2013 | Merli | |
| 9,011,291 B2 | 4/2015 | Birrell | |
| 2002/0042328 A1 | 4/2002 | Yoo | |
| 2004/0224825 A1 | 11/2004 | Giannelli et al. | |
| 2004/0248709 A1 | 12/2004 | Rodgers, Jr. | |
| 2004/0259692 A1 | 12/2004 | Martin et al. | |
| 2006/0287617 A1 * | 12/2006 | Taub | A61H 1/02 601/24 |
| 2007/0087906 A1 | 4/2007 | Rodgers, Jr. | |
| 2007/0087907 A1 | 4/2007 | Rodgers, Jr. | |
| 2007/0184953 A1 * | 8/2007 | Luberski | A63B 22/18 482/146 |
| 2007/0232457 A1 | 10/2007 | Porth | |
| 2008/0064572 A1 | 3/2008 | Nardone | |
| 2008/0171636 A1 * | 7/2008 | Usui | A63B 24/0062 482/8 |
| 2009/0131225 A1 * | 5/2009 | Burdea | A63B 21/06 482/5 |
| 2009/0156369 A1 | 6/2009 | Rodgers, Jr. | |
| 2009/0298649 A1 * | 12/2009 | Dyer | A63B 22/001 482/4 |
| 2010/0167878 A1 | 7/2010 | Grind | |
| 2010/0210421 A1 * | 8/2010 | Case, Jr. | A63B 24/00 482/8 |
| 2010/0304932 A1 | 12/2010 | Kolman et al. | |
| 2011/0003665 A1 | 1/2011 | Burton et al. | |
| 2011/0077129 A1 * | 3/2011 | Martens | A63B 22/00 482/8 |
| 2011/0112441 A1 | 5/2011 | Burdea | |
| 2011/0300994 A1 * | 12/2011 | Verkaaik | A61H 1/0274 482/51 |
| 2012/0015779 A1 | 1/2012 | Powch et al. | |

\* cited by examiner

EXERCISE DEVICE PATH TRACES

CROSS-REFERENCE TO RELATED PATENT APPLICATIONS

The present application is a continuation application claiming priority under 35 USC Section 120 from co-pending U.S. patent application Ser. No. 13/371,014 filed in Feb. 10, 2012 by James S. Birrell and entitled EXERCISE DEVICE PATH TRACES, the full disclosure of which is hereby incorporated by reference.

The present application is related to co-pending U.S. patent application Ser. No. 11/646,882 filed on Dec. 28, 2006 by Jonathan M. Stewart, Rodney P. West, David E. Dyer, James S. Birrell and Sean Horita and entitled END OF TRAVEL STOP FOR AN EXERCISE DEVICE, the full disclosure of which is hereby incorporated by reference.

The present application is related to co-pending U.S. patent application Ser. No. 11/646,850 filed on Dec. 28, 2006 by Victor Pipinich, Robert Silbernagel and Sean Horita and entitled METRIC DISPLAY FOR EXERCISE EQUIPMENT, the full disclosure of which is hereby incorporated by reference.

The present application is related to co-pending U.S. Pat. No. 7,758,469 issued on Jul. 20, 2010 by David E. Dyer; Sean Horita; James S. Birrell; Rodney P. West; and Jonathan M. Stewart; and entitled EXERCISE DEVICE VISUAL REPRESENTATION, the full disclosure of which is hereby incorporated by reference. The present application is related to U.S. patent application Ser. No. 13/087,292 filed on Apr. 14, 2011 by Jonathan M. Stewart, David E. Dyer and Peter J. Arnold and entitled EXERCISE APPARATUS WITH FLEXIBLE ELEMENT, the full disclosure of which is hereby incorporated by reference

BACKGROUND

Exercise devices having a limited and controlled path of motion may become monotonous to use over time. Some exercise devices may provide a greater degree of freedom of motion. However, existing exercise devices do not fully take advantage of such freedom of motion to fully engage persons exercising to enhance the overall exercising experience.

DETAILED DESCRIPTION OF THE EXAMPLE EMBODIMENTS

Figure 1:
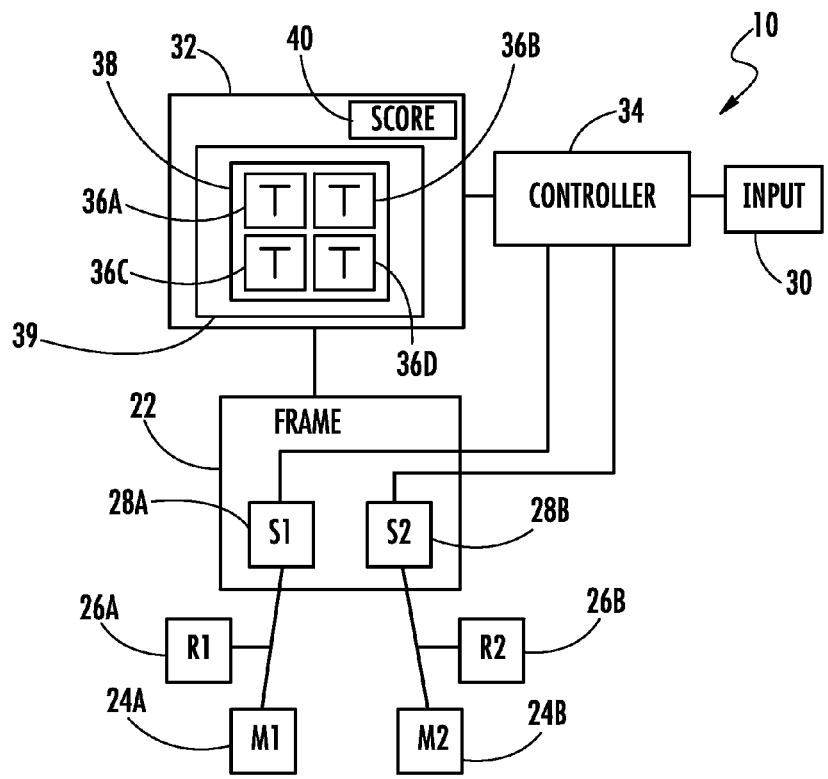
FIG. 1 is a schematic illustration of an exercise device according to an example embodiment.

FIG. 1 schematically illustrates an exercise device 10 according to an example embodiment. Exercise device 10 provides a person exercising (the user) with a multitude of different available paths and a greater degree of freedom of motion. As will be described in more detail hereafter, exercise device 10 further provides feedback in the form of a visual representation of the particular paths taken by the user. In particular, exercise device 10 concurrently presents a plurality of visible tracings on a display, each of the visible tracings being based upon one of a plurality of available paths actually taken by a member of an exercise device. As a result, exercise device 10 makes visible a collective representation of all the chosen paths and their characteristics during a workout, providing the person exercising with a more complete experience.

As shown by FIG. 1, exercise device 10 includes frame 22, members 24A, 24B (collectively referred to as members 24), resistance supplies 26A, 26B (collectively referred to as supplies 26), sensors 28A, 28B (collectively referred to as sensors 28), input 30, display and 32 and controller 34. Frame 22 comprises one or more structures which serve as a base or foundation for remaining components of exercise device 10. Frame 22 movably supports members 24 such that each of members 24 may move in a multitude of different paths or ranges of motion. Towards this end, frame 22 may include one or more joints, bearings, elastic members or other structures that facilitate movement of each of members 24 through or along a plurality of different paths or to different extents.

In one embodiment, frame 22 movably supports each of members 24 through a continuous and endless path such as a circle, oval (ellipse), or polygonal path or other curved or irregular path. In another embodiment, frame 22 may movably support members 24 along multiple paths having distinct endpoints, wherein the endpoints are at different locations in space. For example, in one embodiment, members 24 may be supported so as to reciprocate or move back and forth along a linear segment, along an arcuate segment or along a complex segment having multiple twists and turns, wherein each segment has two distinct endpoints.

In one embodiment, frame 22 may movably support members 24 for movement along a substantially infinite number of paths which may differ from one another in two or more axes. For example, frame 22 may permit a user to take any of a continuum of paths for one or both of members 24 across a range of space. In another embodiment, frame 22 may movably support each of members 24 along paths which are predefined and which differ from one another by predetermined degrees.

Members 24 comprise structures extending from or supported by frame 22 that are configured to receive force applied by the user to effectuate exercise. Members 24 are further configured to use the force applied during exercise to move relative to frame 22 to almost instantaneously change between different available paths with respect to frame 22 in response to force applied by a person to one or more of members 24. For example, in one embodiment, members 24 may be configured to exercise a person's lower extremities such as his or her legs. During such exercise, the person exerts a force with his or her legs against members 24 which results in members 24 moving through a selected path. By simply changing the amount of force or the direction of force applied to members 24 by his or her legs, a person may change the actual path taken by members 24 relative to frame 22. For example, a person may move his or her legs in a more forward or reverse direction to increase or decrease a stride length, or up and down to increase or decrease a jogging, running, stepping or climbing motion. Such changes may occur solely in response to the force applied by person's legs to members 24 during exercise. In other words, person does not need to actuate a separate control to change the paths along with members 24 moved along which the person's legs move. The user-defined path or user-defined motion may be controlled solely in response to force applied by the same portion of a person that is exercising during exercise. In a similar fashion, members 24 may also or alternatively be configured to change between different paths in response to forces or the direction of forces applied to members 24 by other portions of a person's anatomy being exercised and which move with members 24 through one of a plurality of available paths during exercise. A person may enter commands to input 30 to also change a vertical height of the path of members 24.

In one embodiment, members 24 may comprise foot links, footpads, pedals and/or steps configured to be engaged or pressed upon by a user's feet. In such an embodiment, members 24 may be elevated above a supporting floor or ground by frame 22. In such an embodiment, because members 24 receive force applied by a user's feet, members 24 are adapted to facilitate exercise of a user's legs or lower extremities. The path along which members 24 travel varies in response to force or the direction of force applied to members 24 by the user's legs and feet.

In one embodiment, members 24 may comprise bars, grips, arm links or other structures configured to be pressed upon by a person's hands or arms. For example, members 24 may be configured to be grasped by user's hands such that members 24 are moved upon application of force by the user's arms. Members 24 may alternatively be configured to be pressed upon by user's forearms, facilitating exercise of a user's arms. The path along which members 24 travel varies in response to force or the direction of force applied to members 24 by the user's arms, such as his or her forearms.

In one embodiment, members 24 comprise relatively rigid structures rigidly extending from frame 22 which movably support members 24. In other embodiments, members 24 may include flexible or elastomeric portions extending from frame 22. In some embodiments, members 24 may themselves include one or more articulating or pivoting joints. In yet another implementation, members 24 may comprise an endless belt on a treadmill with incline and speed adjustments or stride length sensors built into the treadmill.

Resistance supplies 26 comprise mechanisms configured to supply or apply resistance to movement of members 24 along the taken path. For example, a first resistance supply can resist horizontal motion and a second resistance supply can resist vertical motion. In the embodiment illustrated, resistance supplies 26 supply a user selectable or user controllable degree or amount of resistance against movement along the taken path. In one embodiment, each of resistance supplies 26 may apply a varying amount of resistance through the different degrees or levels of friction such as with one or more friction brakes. In another embodiment, each of resistance supplies 26 may apply a varying amount of resistance through the use of different members having different elasticities. In yet another embodiment, each of resistance supplies 26 may create resistance through the use of one or more electrical or magnetic fields. For example, resistance supplies 26 may comprise generators having magnets, wherein movement through a magnetic field is resisted and wherein such resistance is adjustable. In another embodiment, resistance supplies 26 may include fan blades and the like which are adjustable to provide different degrees of resistance as the blades move through air. In still other embodiments, resistance supplies 26 may have other configurations.

Sensors 28, input 30, display 32 and controller 34 each serve as part of a feedback system regarding the path taken by members 24. Sensors 28 comprise mechanisms configured to detect or sense the path selected by the user and taken by members 24 in response to the application of force to members 24 by the user. In one embodiment, sensors 28 may comprise one or more optical detectors such as one or more optical emitters and detectors. In another embodiment, sensors 28 may comprise individual cameras configured to detect movement of members 24 in space. In other embodiments, sensors 28 make comprise other mechanisms configured to detect and track movement of members 24, such as, for example, one or more accelerometers. Other examples of motion detectors or sensors, include, but are not limited to: sound (acoustic sensors), opacity (optical and infrared sensors and video image processors), geomagnetism (magnetic sensors, magnetometers), reflection of transmitted energy (infrared laser radar, ultrasonic sensors, and microwave radar sensors), electromagnetic induction (inductive-loop detectors), and vibration (triboelectric, seismic, and inertia-switch sensors).

Input 30 comprises one or mechanisms configured to permit the entry of selections, commands and/or data into exercise device 10. In one embodiment, input 30 may be configured to facilitate entry of such selections, commands or data by the user of exercise device 10. For example, in one embodiment, input 30 may comprise a touchpad, a touch screen, a keyboard, a mouse, one or more dials, one or more pushbuttons: one or more rocker switches or a microphone and appropriate voice recognition software. In other embodiments, input 30 may also, or alternatively, include an electronic plug-in or port configured to receive selections, commands and/or data from an external electronic device. In yet another embodiment, the input 30 may comprise an input device configured to receive selections, commands and/or data, wherein such input is transmitted to exercise device 10 across the Internet or an intranet in a wired or wireless fashion.

Display 32 comprises a monitor, screen or other device configured to present visual information to a user of exercise device 10 while the user is exercising. For example, display 22 may comprise an LCD screen. In another embodiment, display 32 may comprise an array or series of individual lights or light emitting diodes that are selectively illuminated to provide visual information. In one embodiment, display 32 may be a part of a touch screen which also serves as input 30.

In one embodiment, display 32 is fixedly mounted to frame 22 and supported such that a person may view display 32 when exercising. In yet another embodiment, display 32 may be provided by a portable device which is removably connectable to exercise device 10. For example, display 32 may be provided by a hand held personal data device such as a tablet (IPAD), personal digital assistance (PDA), portable media player (such as an IPOD), MP3 player or similar portable device having a display which is connected to controller 34 via a plug-in or port or wirelessly, wherein the portable device is supported by frame 22 during such exercise or is held by the user exercising.

Controller 34 comprises one or more processing units configured to receive signals from sensors 28, to receive selections, commands or data from input 30 and to generate control signals directing the operation of at least display 32 and potentially additionally directing the operation of frame 22 and resistance supplies 26. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 34 may be embodied as part of one or more application-specific integrated circuits (ASICs). Unless otherwise specifically noted, the controller is not limited to any specific combination of hardware circuitry and software, nor to any particular source for the instructions executed by the processing unit.

In the embodiment illustrated, controller 34 generates control signals based upon signals received from sensors 28 that cause display 32 to operate in a mode in which display 32 concurrently presents or displays a plurality of visible tracings 36A, 36B, 36C and 36D (collectively referred to as tracings 36), wherein each of the plurality of visible tracings 36 has a shape or configuration based upon the path through which members 24 move as selected by the person exercising. Rather than displaying only one tracing at a time representing the current path being taken, controller 34 causes display 32 to present multiple tracings 36 which represent multiple paths that have been completed. As a result, these tracings 36 provide the person exercising with a composite drawing or mosaic 38 visibly and graphically representing the range and diversity of the motions or paths completed during an exercise session. The composite image of tracings allows the person exercising to evaluate the diversity of paths completed, wherein the diversity of paths corresponds to the diversity of muscle motions that have been completed. The composite image 38 formed by the collection of traces 36 further allows a person to more appropriately adjust his or her paths of motion to alter the composite image 38 being drawn or imaged to achieve a wider range of exercise motions to develop enhanced flexibility and strength in multiple ranges of motion.

For purposes of this disclosure, the term "visible trace" or visible tracing" shall refer to any line or series of markings presented positively or negatively. A "positive" line or marking is where the line or marking is added to and is visible upon the background, whereas a "negative" liner marking is where the liner marking is formed by removing portions of the background such that the line or marking is visible as defined by edges of the remaining background (such as where a target shape is being erased by the tracings).

As further shown by FIG. 1, in the example illustrated, controller 34 is also configured to generate control signals causing display 32 to present a target shape 39. The shape 39 graphically represents a boundary area that defines a target or goal of a range of exercise motions or paths to be completed during one or more exercise sessions on exercise machine 32. In other words, shape 39 graphically represents group or set of different paths to be completed during one or more exercise sessions on exercise machine 32. The target shape 39 may be chosen based upon input from a user via input 30 or based upon an exercise routine, exercise program or exercise objectives selected by a user, a trainer or some other source and entered via input 30 or contained in the memory of an exercise computer program or the like. The target shape may be a closed curved shape, a generally polygonal shape, rectangular, elliptical, ovoid, square, circular, oval, irregular and combinations thereof.

In one embodiment, target shape 39 comprise a target shape or outline to be filled in by traces 36. The person exercising is encouraged to control or adjust the paths taken by members 24 so as to cause display 32 to present a collection of traces 36 that substantially fills the outline or target shape 39. In one embodiment, controller 34 compares the collection of traces 36 to target shape 39 to generate a score 40 which presented on display 40. One of more factors, such as the time utilized to fill in the target shape 39 by a predetermined percentage, accuracy-extent to which the tracings extend outside the target shape 39, difficulty of the target shape 39 or efficiency, the extent to which traces overlap or are coincident, may be utilized to score a particular image 38. Such scores as well as the resulting images 38 and the target shape 39 may be stored for subsequent review.

In another embodiment, target shape 39 may comprise a substantially filled in or solid shape or image to be covered using traces 36. The person exercising is encouraged to control or adjust the paths taken by members 24 so as to cause display 32 to present a collection of traces 36 that substantially covers the target shape 39. In one embodiment, controller 34 compares the collection of traces 36 to target shape 39 to generate a score 40 which presented on display 40.

In yet another embodiment, target shape 39 comprises a substantially filled in or solid shape or image that is to be erased using generated traces 36. In such an embodiment, each individual trace erases a part of the target shape 39. The person exercising is encouraged to complete different paths a motion so as to generate different traces 36 which, trace by trace, erase the displayed target shape 39. In such an embodiment, the traces 36 are positively displayed on top of the target shape 39 or are displayed as generated voids in the target shape 39 (the shape of the void erasing a portion of the target shape 39 corresponding to the shape of the trace).

By completing (or erasing) the target shape 39, a person may have exercised a variety of muscle groups or moved his or her legs or body in a variety of different paths to achieve a desired workout. In one implementation, particular portions of a target shape 39, such as a particular corner, may only be completed (or erased) under predefined circumstances, conditions or modes of operation. For example, in one implementation, one corner of a target shape 39 may be completed or erased if the exercise device (say for example, a treadmill) is operated a 5 degree angle at a speed of 8.0, while another quarter portion of the target shape 39 daily be completed if that type of device (i.e. treadmill) is operated at a 10° angle at a speed of 6.0. By way of another example, a particular portion of a target shape 39 may only be completed if an exercise device (for example, an elliptical device) is operated at a cross ramp setting of nine with resistance level of five.

In one implementation, the person exercising is notified as to what combination of exercise settings or parameters will fill in the corresponding particular portion of the target shape 39. Such indications may be provided by text within or overlaid upon the target shape itself, may be provided alongside of the screen or target shape or may be provided by various color coding and the like. In yet other implementations, the person exercising may be required to search and explore what parameters (inclinations, resistances, speeds, durations, path shapes or the like) will actually fill in particular portions of the target shape 39.

In other embodiments, target shape 39 may be omitted, wherein the person exercising may simply create his or her own unique image 38. As a result, the person exercising is allowed some extent of free styling and creativity to create unique designs and images. Such designs may be stored for later viewing or printing.

Although FIG. 1 illustrates exercise device 10 as having two members 24, two resistance supplies 26 and two sets of sensors 28, facilitating interaction with two legs or two arms of a person exercising, in other embodiments, exercise device 10 may alternatively include a single member 24, is in the resistance supply 26 and a single group of sensors 28. For example, exercise device 10 may have a single member 24 which is engaged by only one arm or one leg. Exercise device 10 alternatively be configured such that a single member 24 is engaged by both arms are both legs. For example, exercise device 10 may simulate ski boarding where both legs engaging single member. Although exercise device 10 is illustrated as having dedicated groups of resistance supplies 26 and groups of sensors 28 dedicated to each member 24, in other embodiments, more than one of members 24 may share the same resistance supply 26 or the same group of sensors 28.

Figures 2, 3:
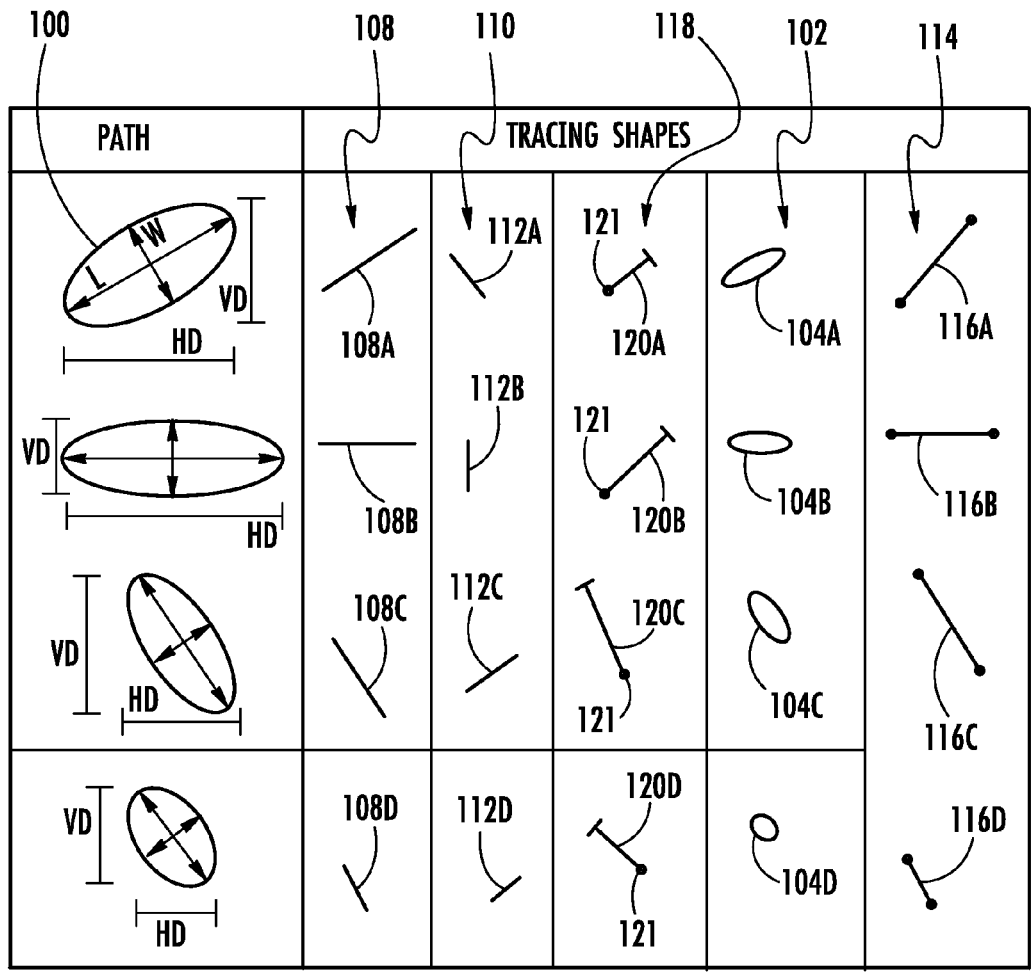
FIG. 2 is a chart illustrating different examples of motion paths and corresponding examples of tracing shapes for display by the exercise device of FIG. 1.
FIG. 3 is a chart illustrating different examples of trace graphic characteristics representing different path characteristics.

FIG. 2 is a chart illustrating different examples of traces 36 based upon different paths of members 28 (shown in FIG. 1). In particular, FIG. 2 illustrates for different available paths 100A, 100B, 100C and 100D (collectively referred to as paths 100) through which members 28 have moved and completed. As shown by FIG. 2, each of paths 100 may be represented by any one of a variety of different tracing configurations or shapes. As shown in column 102, the visible traces 104A, 104B, 104C and 104D have shapes or configurations identical and proportional to their corresponding paths 100A, 100B, 100C and 100D, respectively. In other embodiments, traces 36 may have shapes or configurations based upon a magnitude or orientation of the corresponding path. For example, as shown in column 106, in one embodiment, the visible traces 108A, 108B, 108C and 108D comprise lines or segments with each line or segment having a length corresponding to the length of the path (L) (corresponding to the length of an exerciser's stride in some exercise devices) and an orientation (angular positioning) corresponding to the orientation of the path. For example, as shown in column 110, in one embodiment, the visible traces 112A, 112B, 112C and 112D comprise lines or segments with each line or segment having a length corresponding to the width of the path (W) (corresponding to the vertical extent an exerciser's stride in some exercise devices) and an orientation (angular positioning) corresponding to the orientation of the path. For example, as shown in column 114, traces 36 may comprise line segments having a length corresponding to a horizontal displacement (HD) of the path and an orientation corresponding to the orientation of the path. In yet other embodiments, base 36 may comprise line segments having a length corresponding to the vertical displacement (VD) of the path in an orientation corresponding to the orientation of the path. The traces may have different colors and may be used as a piece of art or souvenir. In one implementation, the FEA may save such completed traces, wherein they may be downloaded to a flash drive or sent it over the internet to be printed out or otherwise saved or used.

In yet other embodiments, as shown by column 118, the shape of traces 36 may be based upon dimensions or orientation of the path in combination with other characteristics of the path. For example, traces 36 may have a length corresponding to either the length (L) or (W) of the path or the vertical displacement or horizontal displacement of the path, wherein the orientation or angle of the tracing shape is dependent upon other factors such as the velocity of members 28 along the particular path, the resistance applied against the movement of members 28 when traversing the particular path or the like. In the example illustrated, traces 120A and 120B represent paths completed in the same time (i.e. with different velocities of members 28), resulting in the orientations or angle of such traces being also substantially the same. The length of such traces 120A and 120B differs due to the different path length (L). Traces 120C and 120C have different orientations corresponding to the different time periods needed to complete the paths. Because traces 120A and 120B have completion times greater than a predetermined threshold time, traces 120A and 120B extend from starting points 121 to the right. Because traces 120C and 120D have completion times less than the predetermined threshold time, traces 120C and 120D extend from starting points 121 to the left.

In addition to having different shapes and lengths depending upon dimensions and orientations of the path being represented or having different shapes or lengths depending upon other characteristics of the path, traces 36 may themselves have different non-shape characteristics based upon the other characteristics of the path. As shown by FIG. 3, different traces being concurrently displayed by display 22 may have different thicknesses, wherein traces 36 have such different thicknesses due to different resistance levels against movement of the first member during the path, different velocities of the first member during the path, and different numbers of repetitions of the represented path during the one or more exercise sessions.

Different path characteristics may also be represented in the traces 36 by different graphic patterns. Different traces 36 being concurrently displayed may be formed from different graphic patterns. For example, traces 36 may be formed by different series of different graphic elements such as x's, o's, *s and the like. Traces 36 may have different graphic patterns based upon different resistance levels applied against movement of the first member during the path, different velocities of the first member during the path, and different numbers of repetitions of the represented path during the one or more exercise sessions. For example, movement of member 28 through a particular path 100 at a first resistance applied by resistance members 26 may have a trace 36 formed by a first graphic pattern while movement of member 28 through a different path 100 at a second different resistance applied by resistance members 26 may have a different trace 36 formed by a second graphic pattern different than the first graphic pattern.

Different path representatives may also be represented in the traces 36 by different colors or brightness levels. Traces 36 may have different colors or different brightness levels based upon different resistance levels applied against movement of the first member during the path, different velocities of the first member during the path, and different numbers of repetitions of the represented path during the one or more exercise sessions. For example, movement of member 28 through a particular path 100 at a first resistance applied by resistance members 26 may have a trace 36 having a first color (red, green or blue for example) while movement of member 28 through a different path 100 at a second different resistance applied by resistance members 26 may have a different trace 36 formed by a second graphic pattern having a different color. Movement of member 28 through a particular path 100 at a first velocity may have a trace 36 having a first color of movement of member 28 through the same path or a different path 100 at a second different velocity may have a second different color.

In some embodiments, multiple path characteristics may be simultaneously represented in a single trace. For example, the resistance applied against member 28 by resistance sources 26 may be represented by the thickness of a trace while the velocity a member 28 while traversing the path may be represented by the graphic pattern or color of the trace. The shape of the trace may still be based upon the shape or orientation of the path itself.

In the example illustrated, controller 34 is configured to provide the person exercising with a choice amongst various modes of operation for exercise device 10. For example, controller 34 is configured to allow the person to choose whether or not to use a target shape 38 or to freelance (i.e. no target shape is provided). Controller 34 is further configured to allow a person to choose or select what trace non-shape characteristics represent what path non-shape characteristics (whether thickness is used to represent velocity or resistance, whether color or brightness is used to represent velocity or resistance and the like). Controller 34 may also allow the person exercising to select how tracing shapes correspond to the completed paths of members 28 (which of the shaping rules discussed above with respect to columns 106, 110, 114 and 118 or what other rules or formulas used to convert a sensed path to a particular tracing shape being displayed).

Figure 4:
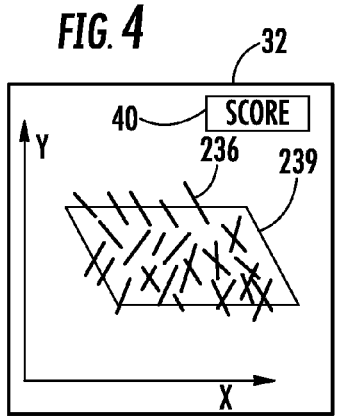
FIG. 4 is an elevational view of one example display of exercise device of FIG. 1.
Figure 5:
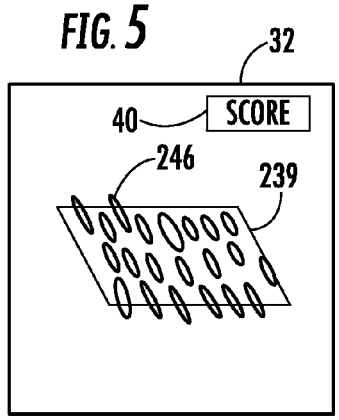
FIG. 5 is an elevational view of another example display of exercise device of FIG. 1.
Figure 6:
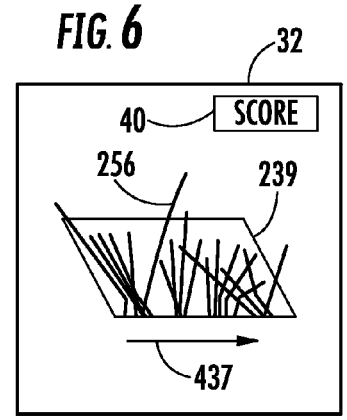
FIG. 6 is an elevational view of yet another example display of exercise device of FIG. 1.

FIGS. 4-6 illustrate example presentations on display 32 produced under the control of controller 34 during different workout sessions. For purposes of this disclosure, a workout session the period of time during which a person continuously exercises on exercise device 10 without interruption. In the example illustrated, controller 34 is configured to store the image 38 from one workout session, wherein the person exercising may retrieve image 38 at a later time for comparison with subsequently produced images 38 resulting from a different workout sessions. In the example illustrated, controller 34 is configured to also permit the person exercising to combine images 38 from multiple workout sessions into a single display or presentation or to recall a previously created image 38 for the addition of new traces 36 during a subsequent workout session.

According to one embodiment, during a particular workout session, controller 34 causes display 32 to continuously add traces to the visible presentation upon the screen or monitor as paths of motion are sensed and completed. In the example illustrated, controller 34 further provides the person exercising with the option of controlling or selecting particular time periods during an exercise session for which traces 36 based upon paths of motion should be added to the visible presentation. In the example illustrated, input 30 includes a user actuatable actuator.

In one user selectable mode offered by controller 34, actuation of the actuator temporarily interrupts or pauses the otherwise continuous addition of traces 36 to the presentation of display 32. For example, in one embodiment, the actuator may be depressable, wherein while the actuator is depressed, traces 36 are not added to the visible presentation even though the person exercising is still completing paths of motion during the exercise session. In another embodiment, actuator may comprise a toggle switch, wherein the person exercising may toggle between the continuous addition of traces between active and inactive states.

In another user selectable mode offered by controller 34, the continuous addition of traces 36 to the presentation of display 32 only occurs while the user actuatable actuator is actuated. For example, in one embodiment, the actuator may be depressable, wherein only while the actuator is depressed are traces 36 added to the visible presentation. In other words, the default state is one of not adding traces 36 unless the actuator is actuated.

In yet another user selectable mode offered by controller 34, the person exercising may establish settings using input 30, wherein traces 36 are added to image 38 at selected spaced time intervals or selected percentages. For example, the user may establish a setting wherein traces are added to the image 38 once every 2 minutes. A user may alternatively establish a setting wherein only one trace for every three completed paths are added to the image 38 (trace being added for the third, the sixth, ninth etc. completed paths during the exercise session).

In each of the examples illustrated in FIGS. 4-6, controller 34 generates control signals causing display 32 to present a target shape 238, one example of target shape 39 described above. Although illustrated as a parallelogram, target shape 238 may comprise any of a variety of different shapes or designs representing the range of motions being targeted during one or more exercise sessions. Examples of such other shapes include ovals, stars, rectangles and the like.

In the example shown by FIG. 4, the person exercising has completed approximately 29 paths of motion with members 24 (shown in FIG. 1). Each of these paths of motion is represented by display 32 with a trace 236. In the example illustrated, each trace 236 comprises a line segment which has a length and orientation which are functions of the corresponding path. FIG. 2, discussed above, describes several alternative functions for producing trace shapes based upon path characteristics.

In the example illustrated in FIG. 4, the location of each trace 236 in space (in the X and Y directions on display 32) may be established the one of a variety of different criteria or schemes. In one embodiment, controller 34 may allow person exercising to choose what criteria are used for locating each trace 236. In one embodiment, controller 34 may establish a default x-y location for all traces at a predetermined location with respect to target shape 238, wherein the actual location of a particular trace with respect to the default location will vary based upon one or more characteristic of the path relative to a predetermined value.

For example, the default location may be a vertical (y-axis) center point of target shape 239 at a leftward most edge (x-axis) of the target shape 239. As time lapses during a workout session, the X axis location of the traces gradually moves to the right. In one embodiment, as each trace 236 ages from the start of a workout session, the color of the trace may change.

The vertical location of the trace (such as the vertical location of a center point of the trace) will vary depending upon a characteristic of the path, such as a velocity of the members 24 during the particular path relative to a predefined threshold velocity. If the velocity of members 28 during a particular path is greater than the predefined threshold velocity, the vertical location of the corresponding trace may be above the default vertical center point. If the velocity of members 28 during a particular path is less than the predefined threshold velocity, the vertical location of the corresponding trace may be below the default vertical center point.

In other embodiments, this scheme may be rotated 90 degrees, wherein each trace has an initial default location along a lower most edge of target shape 239 at a horizontal center point of target shape 238, wherein the addition of traces 236 overtime during an exercise session gradually moves upward and wherein the X-axis location of each trace relative to the default X axis center point varies depending upon a path characteristic, such as velocity of members 28, relative to a predefined threshold velocity. In yet other embodiments, other default locations, other path characteristics or metrics and even other schemes may be used for establishing the locations of traces 236.

FIG. 5 illustrates display 32 during a different workout session, wherein traces 246 are directly proportional in shape and size to the actual paths that have been completed by members 28. FIG. 6 illustrates display 32 during yet a third workout session, wherein traces 432 comprise vectors having directions and magnitudes based upon characteristics or metrics of the paths that have been sensed and completed by members 28 (shown in FIG. 1). In the example illustrated, each trace 256 has an origin defined by controller 36 along a lower most vertical edge of target shape 239. As time progresses during a workout session, the origin location of each trace 256 moves from left to right as indicated by arrow 437. The magnitude and direction of each trace 256 is based upon one or more path metrics or path characteristics, examples of which include, but are not limited to, path shape, path length or width, path vertical or horizontal displacement, path completion time/velocity, and applied resistance.

As indicated in each of FIGS. 4, 5 and 6, controller 34 compares the collection of traces 236, 246, 256 to target shape 239 to generate a score 40 which presented on display 32. One of more factors, such as the time utilized to fill in the target shape 239 by a predetermined percentage, accuracy-extent to which the tracings extend outside the target shape 239, difficulty of the target shape 239 or efficiency, the extent to which traces overlap or are coincident, may be utilized to score a particular image of traces 236, 246, 256. Such scores as well as the resulting images 38 of traces 236, 246, 256 and the target shape 239 may be stored for subsequent review.

In some implementations, a difficult level may be increased upon the achievement of a score that exceeds a predefined threshold. Increasing such a difficulty level may make it more difficult for a person to achieve a high score by filling in the target shape 239 by a predetermined percentage, controlling the extent to which the tracings extend outside the target shape, the difficulty of the target shape or the extent to which the traces overlap or are coincident. In one implementation, the difficult level may be increased by automatically switching to a more difficult shape to be completed or erased. In another implementation, the difficulty level may be increased by automatically switching to a different trace format. For example, upon a person achieving a score above a predefined threshold, the next exercise may automatically switch to a format wherein the particular tracings have a reduced thickness (lesser line weight).

In some implementations, instead of automatically making such an adjustment to a higher difficulty level, controller 94 may alternatively notify the person exercising that he or she has achieved a higher status or higher-level, authorizing the person to a higher difficulty level. For example, the person exercising may be prompted to enter a command or instruction indicating whether he or she wishes to advance to a higher difficulty level. In some implementations, controller 94 may initially query or prompt input from person about to exercise his or her height, fitness level and other physical characteristics. In some circumstances, controller 94 may consult a database or other external sources for such exerciser physical characteristics. Using such information, controller 94 may select an initial or default target shape 39, may adjust the proportions or size of a target shape depending upon a person's height or natural stride lengths based upon such height characteristics of the person exercising, may adjust the proportion of the area of the target shape 39 required to be filled in or erased, may adjust or handicap how scoring is calculated or may adjust parameters of traces (i.e., shape of the trace, thickness of the trace, proportional length or thickness of a trace with respect to an exercise path, resistance, velocity or the like). As a result, controller 94 may use individual characteristics to customize workout targets or objectives for each individual.

In the example illustrated, such scores 40 are further used as a basis for awarding points. Such points may be redeemable for fitness club products or services or other award sponsored by local or national retailers. In one embodiment, such scores (and associated target shapes and collection of traces/images) may be transmitted to third parties for evaluation or other action. For example, such scores (and associated target shapes and collection of traces/images) may be transmitted to fitness trainers which develop or create new target shapes 39 to further expand or alter the range of motions for exercise sessions for a particular person. Such scores (and associated target shapes and collection of traces/images) may be transmitted to healthcare providers or doctors for evaluation and fitness recommendations. Such scores (and associated target shapes and collection of traces/images) may be transmitted to healthcare insurance providers for analysis, evaluation or awards. In other implementations, such scores (and associated target shapes and collection of traces/images) may be transmitted to a charitable organization for a charitable event or, a team or group organizer tracking a collective goal or to a database or repository to complete a collection of different target shapes or traces/images listed at the repository.

As noted above, in one mode of operation selectable by a person exercising, target shape 239 may be omitted. In such modes, the locations of traces may be determined by controller 34 using the same schemes discussed above except that rather than initial or default location of a trace being at least partially based upon the target shape 239, the initial or default location, from which the actual location of a trace will vary depending upon time lapse or path characteristics as described above, may be some predefined center point or location upon the display screen.

FIGS. 7A-7D illustrate the filling or completion during exercise of yet another example target shape 269 that may be presented on display 32. As shown by such figures, target shape 269 has multiple lobes 271 generally coextensive with a central an intersection 273. Lobes 271 are oriented at different angles with respect to a horizontal. In one implementation, such angles may correspond to different target angles or inclines of the paths along which members 24 are to be moved. In another implementation, such different angles may correspond to different levels of resistance to be applied against the movement of members 24. For example, lobes extending further clockwise from a 12 o'clock position may represent ever-increasing levels of resistance. In yet another implementation, such different angles may correspond to different velocities at which member 24 is moved. As noted above, those characteristics of the exercise which are not represented by the angle of traces 266 or the length of traces 266 may be represented in other manners such as with traces 266 with different colors, brightnesses, thicknesses and the like depending upon such other characteristics.

In the example implementation, some lobes 271 project away from intersection 273 by different extents or different distances. In one implementation, the different distances may correspond to different target lengths or distances for the movement of members 24. For example, a longer target stride may be represented by a longer lobe 271, while a shorter target stride may be represented by a shorter lobe 271. In one implementation, the center point or intersection 273 may correspond to a default median or central position P of a member 24 equally spaced from opposite maximum ends of travel for member 24. In one implementation, movement of member 24 in one direction from intersection 273 creates a trace 266 in one direction from intersection 273 to fill a first lobe and movement of member 24 in another opposite direction from intersection 273 creates a trace 266 in an opposite direction from intersection 273 to fill a second lobe which is largely opposite to the first lobe (angularly spaced from the first lobe by approximately 180 degrees). Depending upon the differing lengths of the lobes 271 that are opposite to one another, the target or objective may demand a greater movement in a forward direction from the central median position P of member 24 as represented by the central point 273 as compared to movement in the rearward direction from the location P, or vice versa. In the example implementation, each of traces to 66 comprise elongate oval shaped loop corresponding to the path of member 24. In other implementations, traces 266 alternatively be represented by any of the trace characteristic shown in FIGS. 3-6.

Figure 7A:
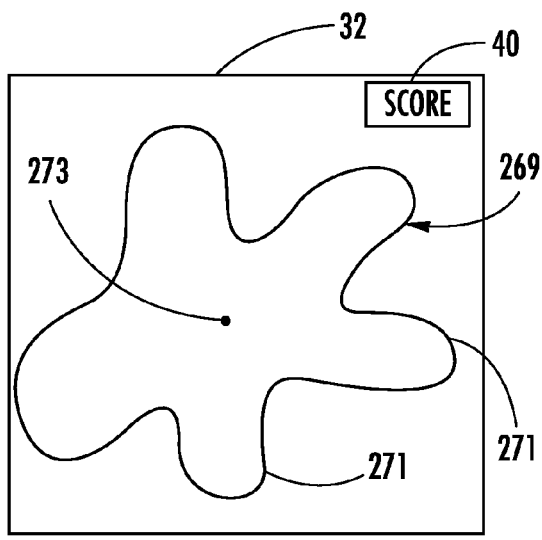
FIGS. 7A-7D illustrate an example target shape graphic being completed with example trace graphics.
Figure 7B:
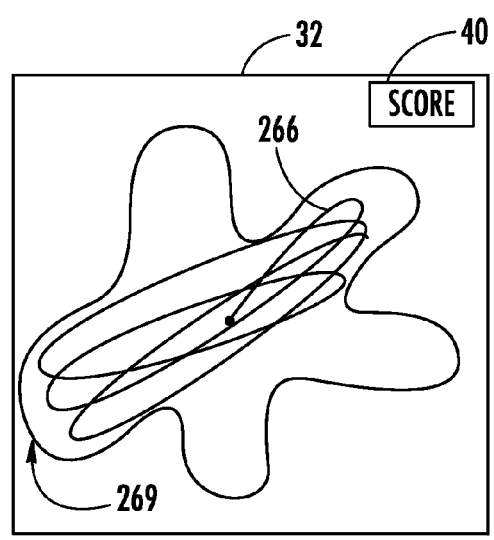
Figure 7C:
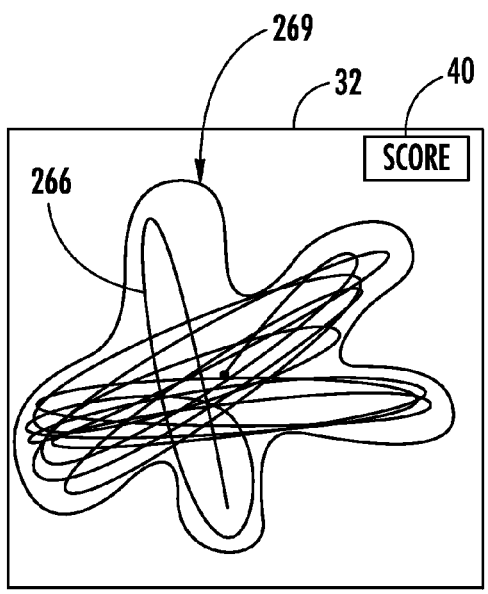
Figure 7D:
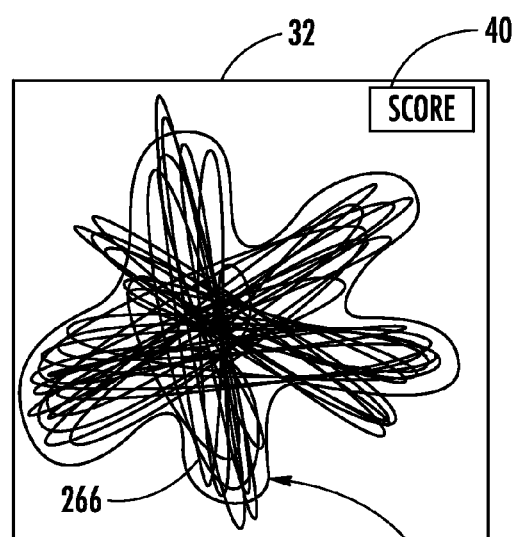

As shown by FIG. 7A, when a person initiates exercise, shape 269 is presented on screen 32 in an incomplete state. In one implementation, shape 269 may be completely empty. In another implementation, shape 269 may be partially prefilled. As shown by FIGS. 7B, 7C and 7D, as the person progresses during exercise, he or she adjusts the shape of the path of members 24 as well other characteristics of members 24, such as resistance, velocity, orientation and the like) to fill the target shape 269. As a result, target 269 provides a visible graphic for encouraging a diverse workout routine or a diverse collection of workout routines. In other implementations, other target shapes may be utilized. Although FIGS. 7A-7D illustrate an example wherein a target shape is filled in, in other implementations, this operation may be reversed, wherein a target shape, such as target shape 269, is opaque and is erased or otherwise modified by traces such as traces 266.

FIGS. 8-14 illustrate exercise device or apparatus 310, a particular example of exercise device 10. Exercise device or apparatus 310 allows a person to adjust a horizontal length of his or her stride simply by the person applying force to foot supports of the exercise apparatus. Exercise apparatus 310 further allows the person to also adjust a vertical length or vertical step height. Exercise apparatus 310 provides such freedom of motion using flexible elements 404 and 406 in an architecture that is compact, less complex and less expensive. In other implementations, exercise device 10 may have different configurations. For example, exercise device 10 may alternatively comprise other presently known or future developed exercise devices. For example, exercise device 10 may alternatively comprise an elliptical machine, a stair stepper machine, a treadmill, a rowing machine, the stationary bicycle and weightlifting or resistance machine and the like.

As shown by FIGS. 8-14, exercise apparatus 310 comprises frame 324, linkage assemblies 326L, 326R (collectively referred to as linkage assemblies 326), swing arms 327R, 327L (collectively referred to as swing arms 327), crank system 328, resistance system 330, coupling systems 334L, 334R (collectively referred to as coupling systems 334), step height adjustment mechanism 338, horizontal resistance system 340 and display 342.

Figure 8:
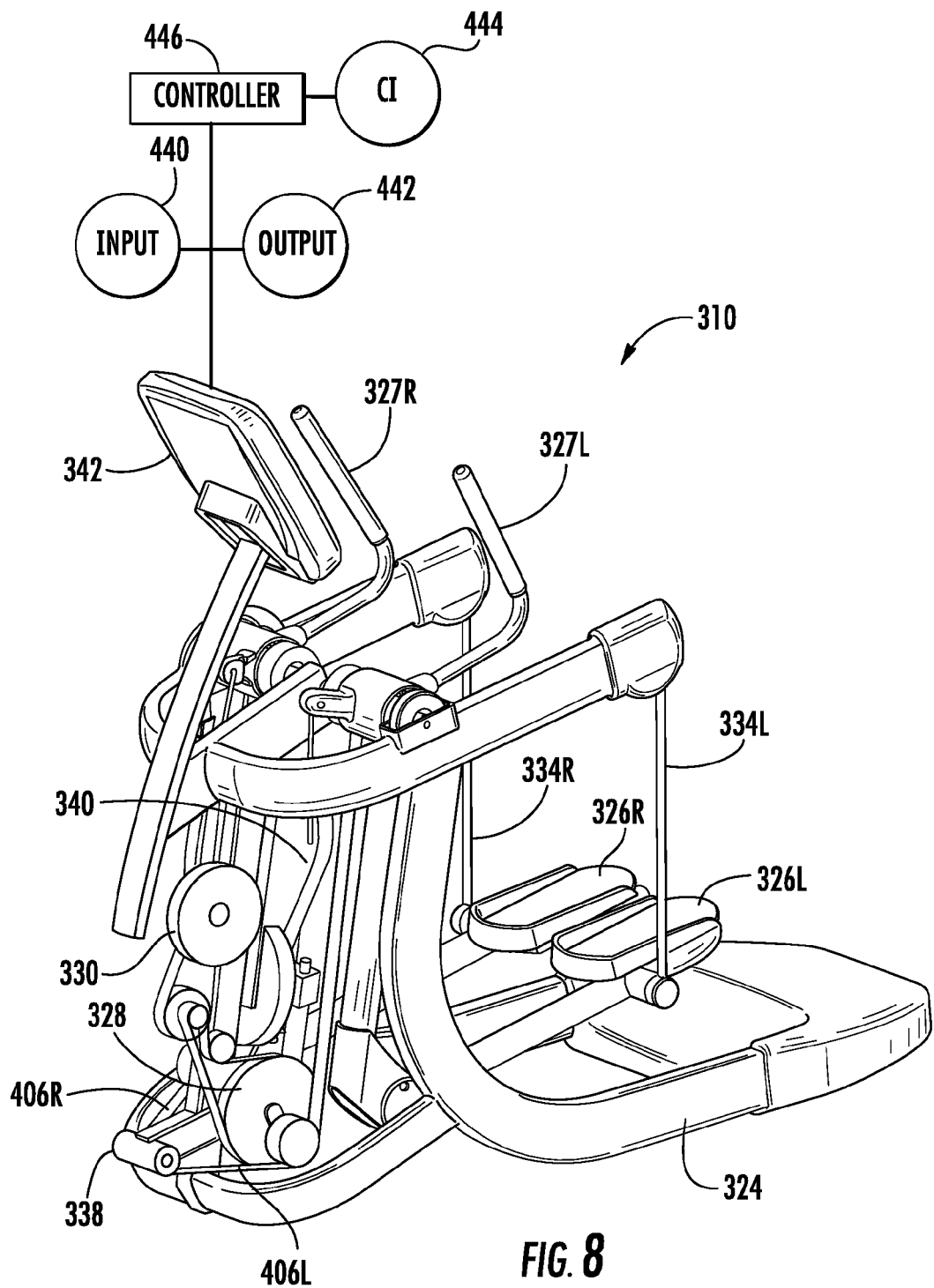
FIG. 8 is a top left perspective view of an example of the exercise device of FIG. 1 according to an example embodiment with portions schematically shown.

Frame 324 supports exercise apparatus 310 upon a base or floor. As illustrated in FIG. 8, frame 324 includes rear base portion 350, front or forward post or leg 352, rear supports or legs 354R, 354L (collectively referred to as rear supports 354), side arms 356L, 356R (collectively referred to as side arms 356), front support 355, front supports 346R, 346L (collectively referred to as front supports 346), front support 347, cross-shaft 349, end caps 351R, 351L (collectively referred to as end caps 351), covers 357R, 357L (collectively referred to as covers 357) and crank support 353. Base portion 350 bears against the floor and is connected to rear supports 354. The bottom of forward post 352 bears against the floor. Forward post 352 extends at a forward end of exercise apparatus 310 and is connected to and supports front support 347. Front support 347 connects to and supports side arms 356 and cross-shaft 349. Front supports 346 connect front post 352 to rear supports 354. Platform 348 connects to rear supports or legs 354 and covers rear support 350. Front support 355 connects to front support 347 and supports display 342. Side arms 356 and front support 347 support cross-shaft 349. Rear supports or legs 354 extend toward the rear end of exercise apparatus 310 and are connected to side arms 356. End caps 351R, 351L (collectively referred to as end caps 351) and covers 361R, 361L (collectively referred to as covers 361) connect to side arms 356.

Side arms 356 extend rearwardly from leg 352 and front support 347 on opposite sides of both linkage assemblies 326. Side arms 356 extend substantially parallel to one another at the same vertical height. Side arms 356 provide bars, beams or shafts by which a person's left and right hands may grasp or rest upon when mounting exercise apparatus 310 or when otherwise not grasping handle portions 366R, 366L (collectively referred to as handle portions) of swing arms 327. Side arms 356 help retain a person on linkage assemblies 326 and on exercise apparatus 310 and reduce the likelihood of a person falling off of exercise apparatus 310. Side arms 356 assist in supporting cross-shaft 349 and portions of coupling systems 334. Side arms 356 further serve as shields about flexible elements of couplings systems 334. End caps 351 and covers 357 cover portions of coupling systems 334 by attachment to side arms 356.

Forward post 352 supports front support 347, crank support 353, resistance system 330, step height adjustment mechanism 338 and horizontal resistance system 340. For ease of illustration, portions of post 352, such as brackets or support plates extending forwardly from post 352 are omitted.

Cross-shaft 349 supports linkage assemblies 326, swing arms 327 and portions of coupling assemblies 334. Front supports 346 provide additional support between front post 352 and rear supports 354.

Crank support 353 supports portions of crank system 328 and portions of step height adjustment mechanism 338. Crank support 353 comprises a plate, beam, bar, channel or similar element firmly attached to the rearward side of front post 352. Crank support 353 also comprises operable attachment elements for portions of crank system 328 and step height adjustment mechanism 338. Such operable attachment elements include shafts, hubs, collars, pins, levers or similar elements to allow for movement of crank system 328 portions and step height mechanism 338 portions around a horizontal centerline 374. In another embodiment, support for portions of step height mechanism 338 may be omitted from crank support 353. In some embodiments, crank support 353 may be attached forward of front post 352 or be supported by other portions of frame 324.

Platform 348 provides a location from which the user of exercise apparatus 310 may mount foot pads 362R, 362L (commonly referred to as foot pads) of linkage assemblies 326.

Linkage assemblies 326 comprise one or more members movably supported by frame 324 and configured to elevate and support a person's feet as the person exercising applies force to such linkage assemblies to move such linkage assemblies relative to frame 324. Linkage assemblies 326 are coupled to one another so as to automatically move 180 degrees out of phase with respect to one another when opposing forces are applied to linkage assemblies 326. The person exercising exerts force on foot pads 362 and foot support members 360, alternating right and left, while also pushing and pulling on linkage assemblies 326 to create the out of phase movement of linkage assemblies 326. In other embodiments, other means of synchronization may be used.

Figure 10:
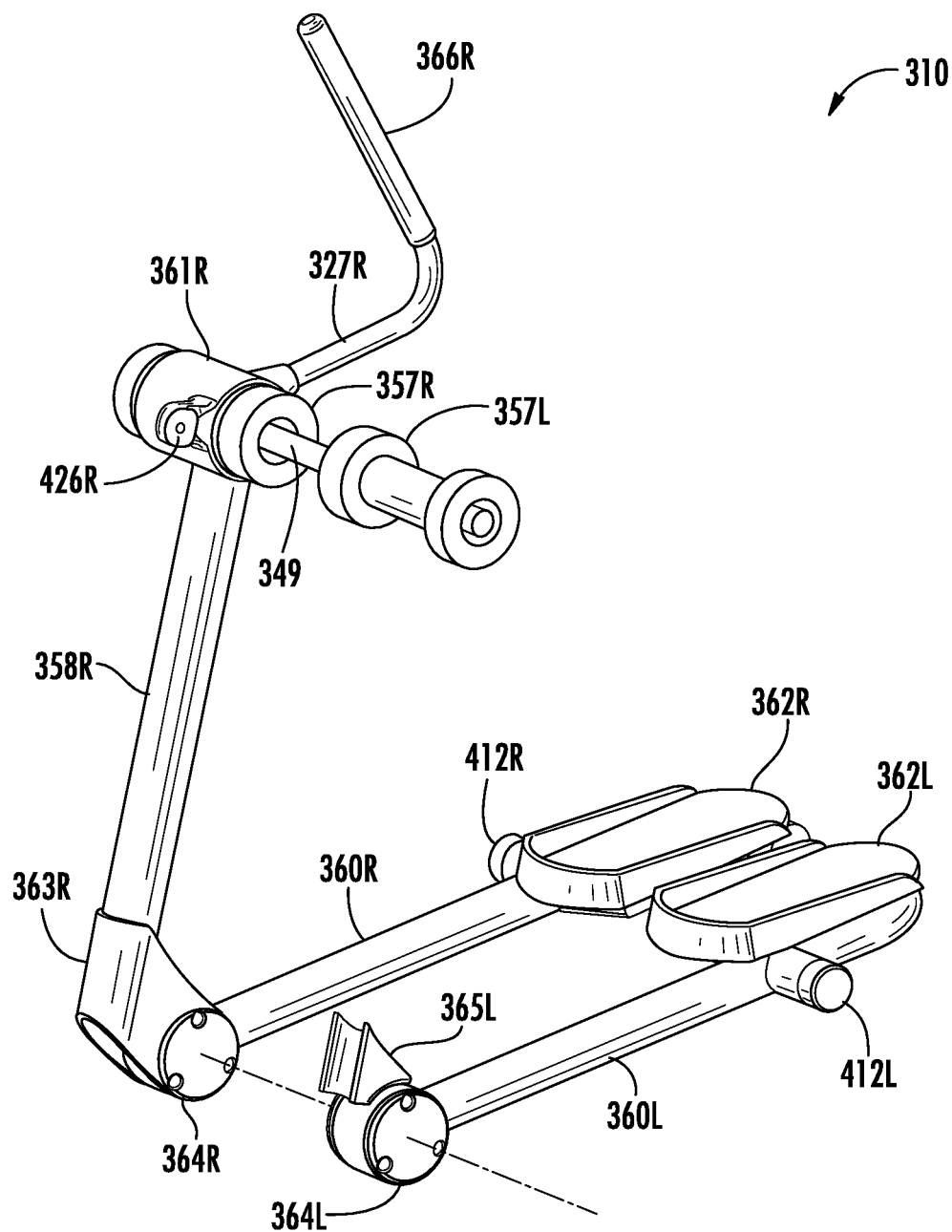
FIG. 10 is another top perspective view of a portion of the exercise device of FIG. 8.

As illustrated in FIG. 10, each of linkage assemblies 326 includes motion members 358R, 358L (collectively referred to motion members 358), torque bars 359R, 359L (collectively referred to torque bars 359), foot support members 360R, 360L (collectively referred to as foot support members 360), hubs 361R, 361L (collectively referred to as hubs 361), foot pads 362R, 362L (collectively referred to as foot pads 362), saddles 363R, 363L (collectively referred to as saddles 363), joints 364R, 364L (collectively referred to as joints 364) and joint covers 365R, 365L (collectively referred to as joint covers 365).

Torque bars 359 are supported by cross-shaft 349. Torque bars 359 are spool-shaped including a center portion of one diameter and end portions of diameters larger than the diameter of the center portion. Each of torque bars 359 includes a circular hole located on its radial centerline and extending along its entire length. The inside diameter of the circular hole is slightly larger than the outside diameter of cross-shaft 349. Torque bars 359 mount on to cross-shaft 349 such as to allow rotational movement of torque bars 359 on cross-shaft 349. The rotational movement of torque bars 359 creates resulting rotational movement or winding and unwinding of portions of coupling systems 334.

Each of hubs 361 is a circular element with a hollow center that is mounted on the smaller diameter portion of one of torque bars 359. Hubs 361 pivotally connect swing arms 327 and motion members 358. The rearward sides of hubs 361 are attached to swing arms 327. The bottom sides of hubs 361 are attached to motion members 358. The forward sides of hubs 361 are attached to portions of coupling systems 334.

Motion members 358 are essentially vertical components that transfer movement from hubs 361 to lower portions of linkage assemblies 326. Motion members 358 are attached to saddles 363 and joint covers 365. Each of saddles 363 wrap around the forward side of the lowest part of one of motion members 358 and are attached to motion members 358. Each of saddles 363 has one or more arms that attach to joints 364. Each of joint covers 365 attach to the rearward side of one of motion members 358 immediately above joint 364. The combination of saddles 363, joints 364 and joint covers 365 pivotally connect motion members 358 to foot support members 360. In other embodiments, motion members 358 and foot support members 360 may be pivotally connected other means such as knee braces, welded hubs or the like.

Each foot support member 360 (also known as a stair arm) extends essentially horizontally from one of joints 364 and supports one of foot pads 362. Each foot pad 362 comprises a paddle, pedal, or the like providing a surface upon which a person's foot may rest. Each foot pad 362 further includes a toe cover or toe clip against which a person's foot or toes may apply force in an upward or vertical direction. Foot pads 362 may have a variety of different sizes, shapes and configurations. In other embodiments, each motion member 358 and foot support member 360 (sometimes referred to as a foot link) may also have different configurations, shapes and connections. For example, in other embodiments, a lieu of foot support member 360 having a rear end which is cantilevered, foot support member 360 may alternatively have a rear end which is pivotally supported by another supporting linkage extending from one of side arms 356 or another portion of frame 324.

Swing arms 327 comprise arms having handle portions 366 configured to be grasped by a person while linkage assemblies 326 are pivoted relative to frame 324. In the example illustrated, swing arms 327 are rigidly connected to hubs 361 which are also rigidly connected to motion members 358. Swing arms 327, hubs 361 and motion members 358 comprise a fixed arrangement that pivots around cross-shaft 349. As a result, swing arms 327 permit a person to exercise his or her arms and upper body. In other embodiments, swing arms 327 may pivot independent of linkage assemblies 326, may have independent resistance systems for exercising the upper body or may be rigidly or stationarily supported by frame 324. In some embodiments, swing arms 327 may be omitted.

Figure 11:
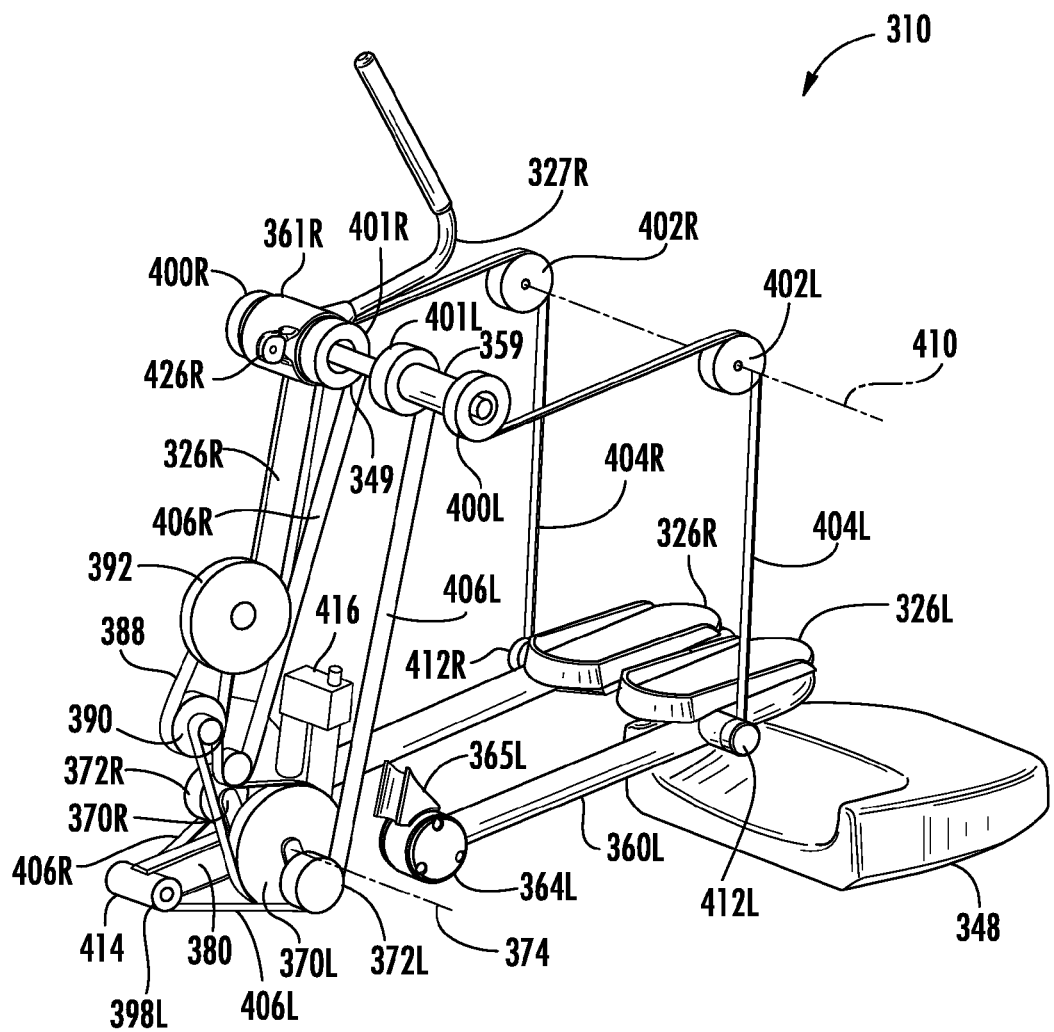
FIG. 11 is another top perspective view of a portion of the exercise device of FIG. 8.
Figure 13:
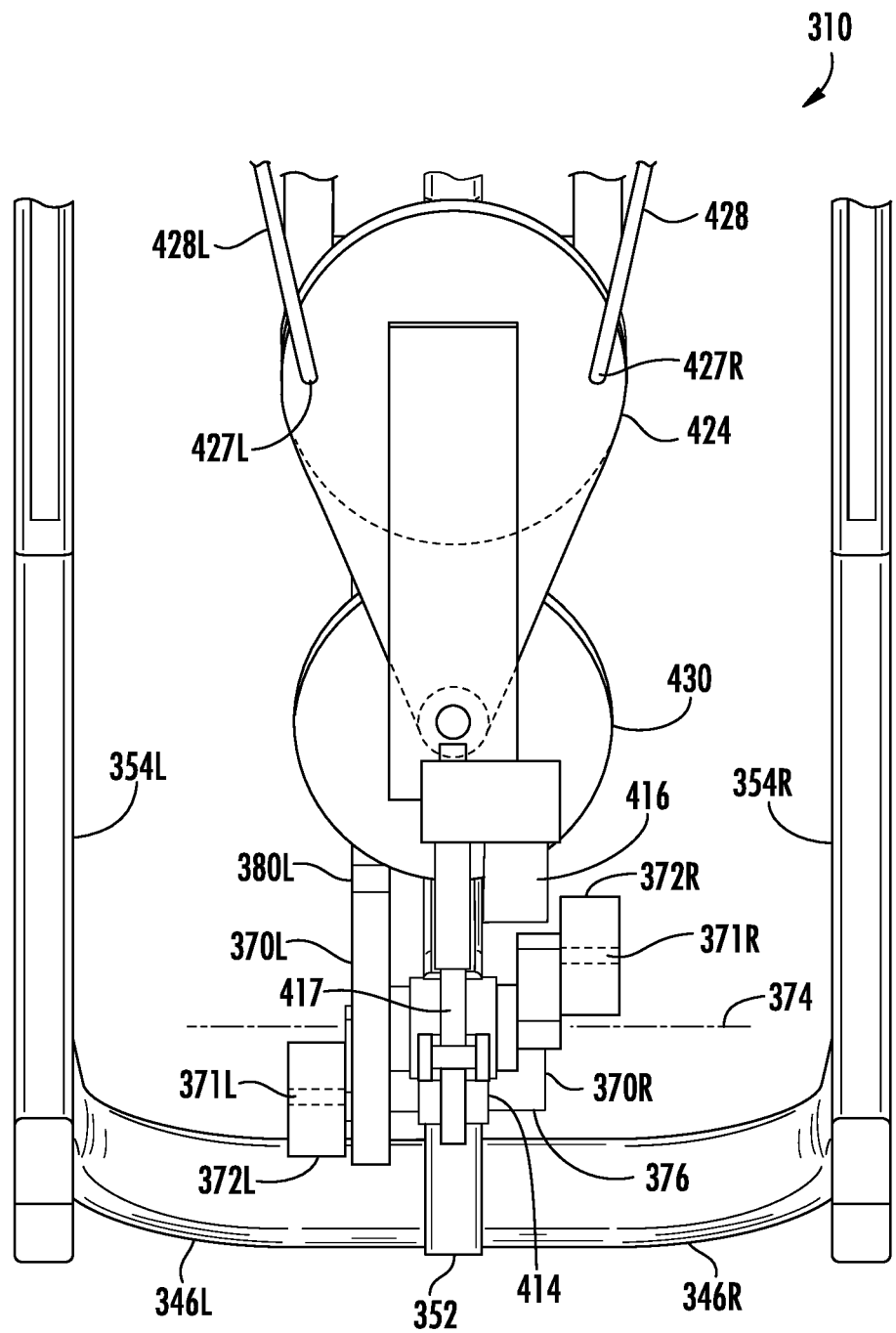
FIG. 13 is a partial rear elevational view of a portion of the exercise device of FIG. 8.

FIGS. 11 and 13 illustrate crank system 328 in more detail. Flexible element portions of coupling systems 334 are omitted from FIG. 22 for ease of illustration. Crank system 328 comprises a mechanism configured to synchronize movement of linkage assemblies 326 and to apply a resistance to such movement. As shown by such figures, crank system 328 crank arms or cranks 370R, 370L (collectively referred to as crank arms 370), crank guide arms 371R, 371L (collectively referred to as crank guide arms 371), flexible element crank guides 372R, 372L (collectively referred to as flexible element crank guides 372) and crank shaft 376.

Cranks 370 transfer force and movement from coupling systems 334 to resistance system 330. Cranks 370 are attached to and supported by crank shaft 376. Crank shaft 376 is supported by crank support 353 in a manner to allow rotation of crankshaft 376 and cranks 370 about horizontal axis 374. Because cranks 370 rotate about a substantially horizontal axis 374 which is positioned near forward post 352, crank system 328 is more compact. In yet other embodiments, crank system 328 may be located elsewhere within the confines of frame 324.

In the example illustrated, crank 370L comprises a combined input crank and sheave in the form of a disk, wheel or the like, wherein the disc or wheel concentrically extends about axis 374. In other embodiments, crank 370L may comprise one or more members configured to rotate about axis 374, wherein crank 370L does not concentrically extend about axis 374. In other embodiments, crank 270L may rotate about a vertical axis in a manner such as illustrated for exercise apparatus 20.

Crank 370R is fixed to crank 370L so as to rotate with crank 370L. In the example illustrated, crank 370R comprises an arm radially extending outward from shaft 376 and supporting guide 372R towards its outer radial end. Crank 370R supports flexible element crank guide 372R attached to crank arm 370R at crank guide arm 371R. Crank 370L includes flexible element crank guide 372L attached to crank arm 370L at crank guide arm 371L.

Crank guide arms 371 and flexible element crank guides 372 are located on crank arms 370 at points that are equidistant and radially spaced from axis 374. The locations of crank guide 372R and crank guide 372L are positioned 180 degrees out of phase from each other. Flexible element crank guides 372 comprise members that are connected to and carried by cranks arms 370 so as to rotate about axis 374 and about which front flexible elements 406 (406R, 406L) of coupling system 334 wrap so as to transmit force to crank guides 372 and ultimately to cranks 370. In the example illustrated, flexible element crank guides 372 comprise a pulley. In other embodiments, flexible element crank guides 372 may alternatively comprise a spool or disc against which a flexible element moves or slides without rotation of the flexible element crank guide 372.

Resistance system 330 applies additional resistance to the rotation of crank system 328. In the particular example illustrated, resistance system 330 provides a selectively adjustable incremental resistance to the rotation of cranks 369 of crank system 328. Resistance system 330 includes belt 380, speed changer 390, belt 388 and resistance source 392. In the illustrated embodiment, speed changer 390 comprises a step up pulley. Belt 380 wraps about one of cranks 369 and the smaller wheel of speed changer 390. Belt 388 wraps about the larger wheel of speed changer 390 and also about the shaft of resistance source 392. The attachment of resistance source 392 to front post 352 adjacent to cranks 369 and with horizontal axis of rotation allows for a more compact and efficient design for exercise apparatus 310. In other embodiments, chain and sprocket arrangements, dear trains and other transmissions may be used to operatively couple cranks 370 to resistance source 392.

Resistance source 392 comprises a mechanism configured to rotate against a selectively adjustable resistance. In one embodiment, resistance source 392 comprises a metal plate and one or more magnets forming an Eddy brake. In one embodiment, the one or more magnets comprise electromagnets, allowing the strength of the magnetic force to be selectively adjusted to control and vary the resistance applied against the rotation of cranks 370. In another embodiment, resistance source 392 may comprise an electric generator. In still another embodiment, resistance source 392 may comprise two surfaces in frictional contact with one another to apply a frictional resistance against rotation of cranks 370. In another embodiment, air brakes may be utilized. In still other embodiments, other brakes or resistance mechanisms may be utilized.

Because resistance system 330 utilizes a two-stage transmission between cranks 369 and resistance source 392, the arrangement or architecture of crank system 328 and resistance system 330 is more compact and the speed ratio between cranks 369 and resistance source 392 (approximately 12:1) provides improved electric performance. In other embodiments, a single stage or a transmission with greater than two stages may be employed. In yet other embodiments, resistance system 330 may have other configurations or may be omitted. For example, in another embodiment, the transmission of resistance system 330 may include gear trains, chains and sprockets or the like.

Figure 8A:
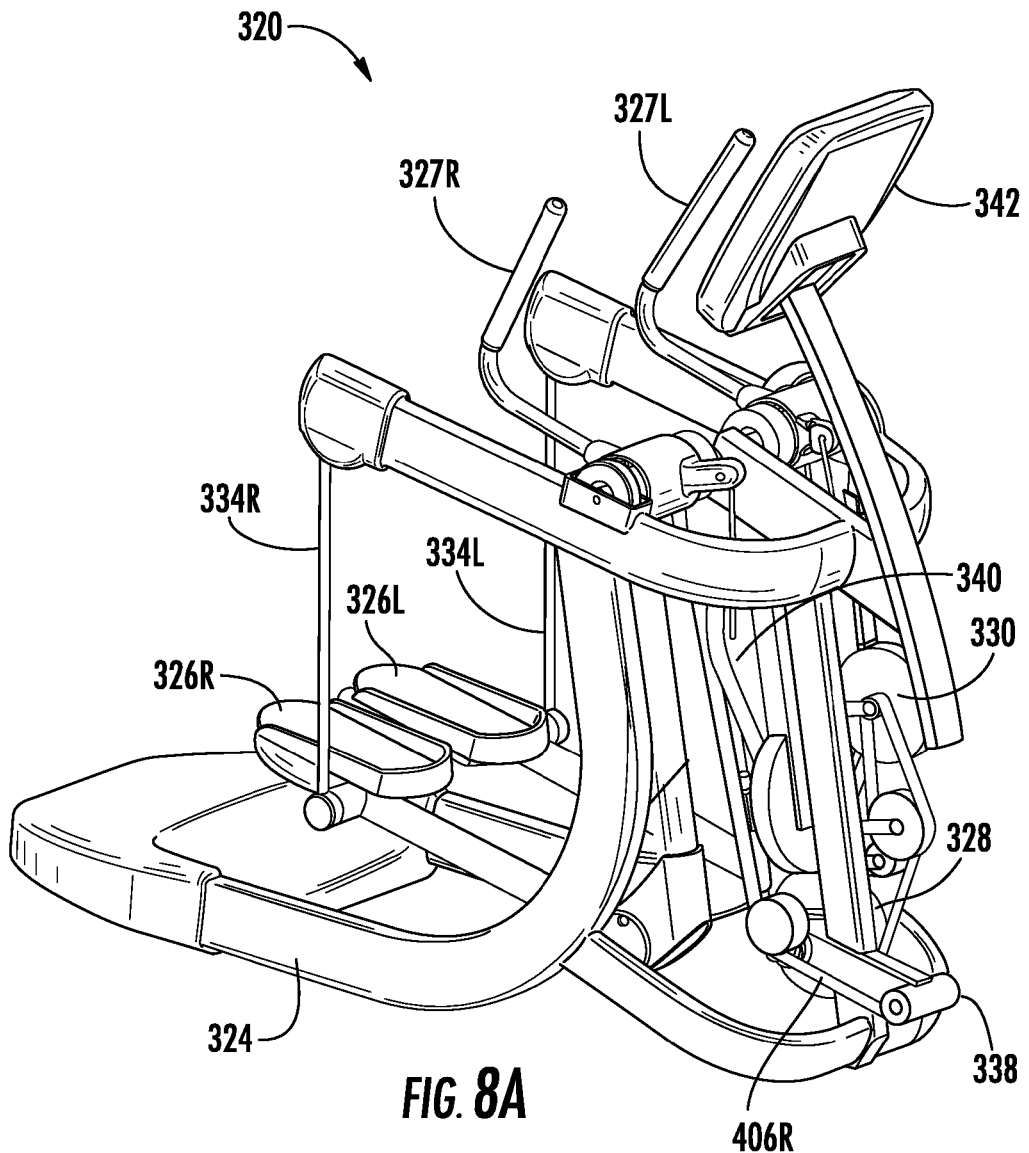
FIG. 8A is a top right perspective view of the exercise device of FIG. 8.
Figure 9:
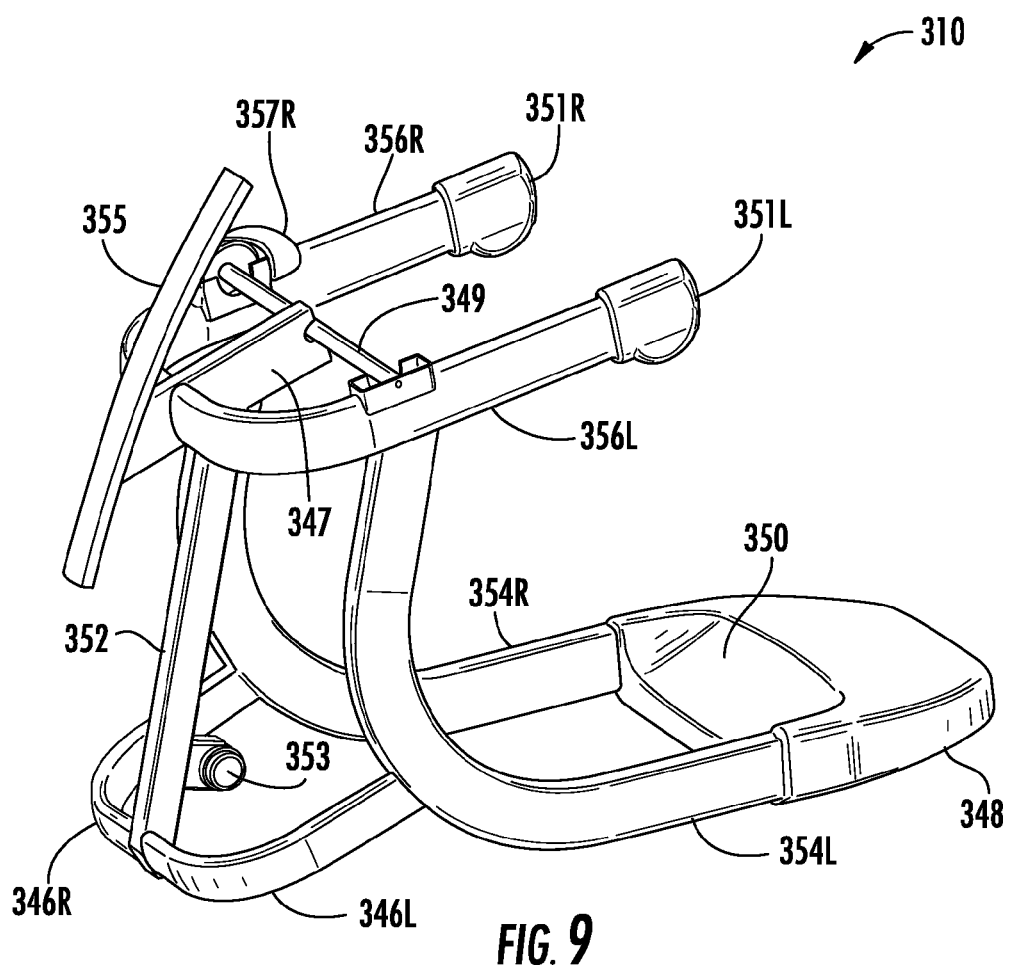
FIG. 9 is another top perspective view of a portion of the exercise device of FIG. 8.

As best shown by FIGS. 8, 8A and 11, coupling system 334 operably couples or joins step height adjustment system 338 to foot support members 360 or footpads 362. Coupling systems 334 include front end flexible element mounts 398R, 398L (collectively referred to as front end flexible element mounts 398), front flexible elements 406R, 406L (collectively referred to as front flexible elements 406), torque bar inboard flexible element mounts 401R, 401L (collectively referred to as torque bar inboard flexible element mounts 401), torque bar outboard flexible element mounts 400R, 400L (collectively referred to as torque bar rear flexible element mounts 404), rear flexible elements 404R, 400L (collectively referred to as rear flexible elements 404), rear guide elements 402R, 402L (collectively referred to as rear guide elements 402 and foot pad flexible element mounts 412R, 412L (collectively referred to as foot pad flexible element mounts 412).

Front flexible elements 406 and rear flexible elements 404 comprise flat belts of fiber reinforced polymer. In one embodiment, elements 404 and 406 comprise Kevlar reinforced polyurethane. Fiber reinforced polymer provides the advantage of durability for flexible elements 404 and 406. In another embodiment, one or more of front flexible elements 406 and rear flexible elements 404 may comprise bendable members such as cables, wires, ropes, belts, cords, strings, chains, and the like. In another embodiment, one or more of front flexible elements 406 and rear flexible elements 404 may comprise belts of materials other than fiber reinforced polymer.

As shown by FIG. 11, front end flexible element mount 398 (also known as a "dead end") comprises a mount or securement point at which an end of front flexible element 406 is attached. In the example illustrated, end mount 398 for each of coupling systems 334 is provided by step height adjustment mechanism 338. In other embodiments in which step height adjustment mechanism 338 is omitted, front end flexible element mount 398 may be provided by part of frame 324. In still other embodiments in which the ends of flexible elements 406 are directly attached to cranks 369 and do not wrap about a flexible elements crank guide 372, end mounts 398 may be provided on cranks 369.

Torque bar inboard flexible element mounts 401 comprise the spool ends of torque bars 359 that are located nearest to the longitudinal centerline of cross-shaft 349. Torque bar outboard flexible element mounts 400 comprise the spool ends of torque bars 359 that are located nearest to the longitudinal ends of cross-shaft 349.

Front flexible elements 406 wrap around flexible elements crank guides 372 and also wrap around from below and toward the rearward side of torque bar inboard flexible element mounts 401. As viewed from the left side of exercise apparatus 310, front end flexible elements 406 wrap around torque bar inboard flexible elements mounts 401 in a counter-clockwise direction. The rearward ends of front flexible elements 406 attach to torque bar inboard flexible element mounts 401. The forward ends of rear flexible elements 404 attach to torque bar outboard flexible elements mounts 400. Rear flexible elements 404 wrap from above and toward the forward side of torque bar outboard flexible element mounts 400 in a counter-clockwise direction as viewed from the left side of exercise apparatus 310. The method of attachment of front flexible elements 406 to torque bar inboard flexible elements mounts 401 and of rear flexible elements 404 to torque bar outboard flexible element mounts 400 serves to laterally transmit torque back and forth between elements 406 and 404 through torque bar 359 in an wind/unwind motion.

A shown by FIG. 10, the torque bar flexible element mounts 400 guide and direct movement of the rear flexible elements 404 to the interior of side arms 356 and toward rear guide elements 402.

In the example illustrated, rear guide elements 402 comprise pulleys rotationally supported by side arms 356 of frame 324 proximate to a rear end of exercise apparatus 310 substantially vertically above footpads 362 when footpads 362 are longitudinally aligned. In other embodiments, each of rear guide elements 402 may alternatively comprise a low friction surface which does not rotate and against which flexible elements 404 moves or slides.

As shown by FIG. 11, each of guide elements 402 further guides and directs flexible element 404 through an opening from an interior of side arm 356 in a substantially vertical direction down to foot support members 360 and footpads 362. In the example illustrated, guide elements 402 rotate about a substantially horizontal axis 410. Although coupling systems 334 are illustrated as having one guide element 402, in other embodiments, coupling systems 334 may alternatively include a greater or fewer of such guide elements.

In the example illustrated, the rearward end of rear flexible elements 404 is fixed to a foot support member 360 by a mount 412 at a location transversely opposite to footpad 362 near or proximate to a forward end of footpad 362. In the example illustrated, each mount 412 includes a body that slides (via screw adjustment) up and down relative to a pivoting block attached to the associated member 360, wherein flexible element 404 is fixed or secured to the body of the mount. Each mount 412 allows the location of members 360 to be adjusted so as to be level with one another. In other embodiments, mounts 412 may comprise other securement mechanisms such as clamps, fasteners and the like. In another embodiment, flexible element 404 may be clamped to mount 412 as described herein for exercise apparatus 20.

Each rear flexible element 404 extends from mount 412 in a substantially vertical direction until engaging rear guide 402. Rear flexible element 404 wraps partially about rear guide element 402 into an interior of one of side arm 356. Rear flexible element 404 extends through the interior of side arm 356 until engaging torque bar outboard flexible element mount 400. Movement is translated from the rear flexible element 404 to the front flexible element 406 through torque bar 359. Front flexible element 406 extends from torque inboard flexible element mount 401 and wraps around flexible elements crank guides 372. Finally, the front end of each front flexible element 406 is secured to one of front end mounts 398.

Because each of coupling systems 334 employs flexible elements (404 and 406) rather than rigid inflexible members or elements, forces may be more smoothly transmitted across convoluted paths, allowing coupling systems 334 and crank system 328 to be more compactly arranged and to be less complex and expensive. In addition, flexible elements (404 and 406) also have a reduced diameter as compared to rigid elements which permits the transmission of forces from linkage assemblies 326 to crank system 328 in even a more compact fashion. In other embodiments, at least segments or portions of front flexible elements 406 or rear flexible elements 404 may alternatively be replaced with rigid inflexible members or elements.

Step height adjustment mechanism 338 is configured to provide foot support members 360 and foot pads 362 with a multitude of different user selectable maximum upper and lower vertical ranges of motion. Adjustment mechanism 338 allows a person to adjust a maximum step height or a maximum step depth of a path through which the left and right foot supports 360 may move.

Figure 12:
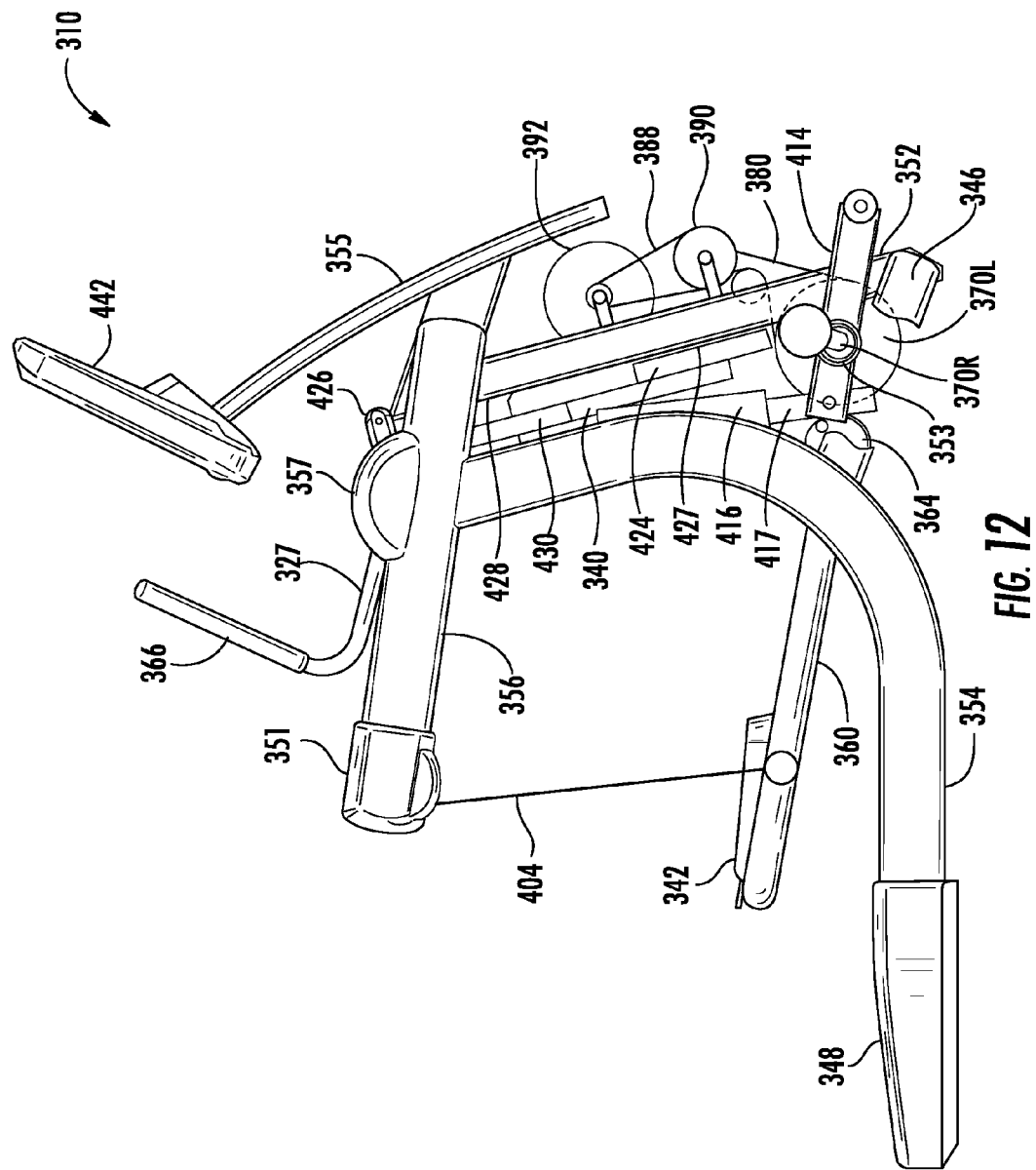
FIG. 12 is a right side elevational view of the exercise device of FIG. 8.
Figure 14:
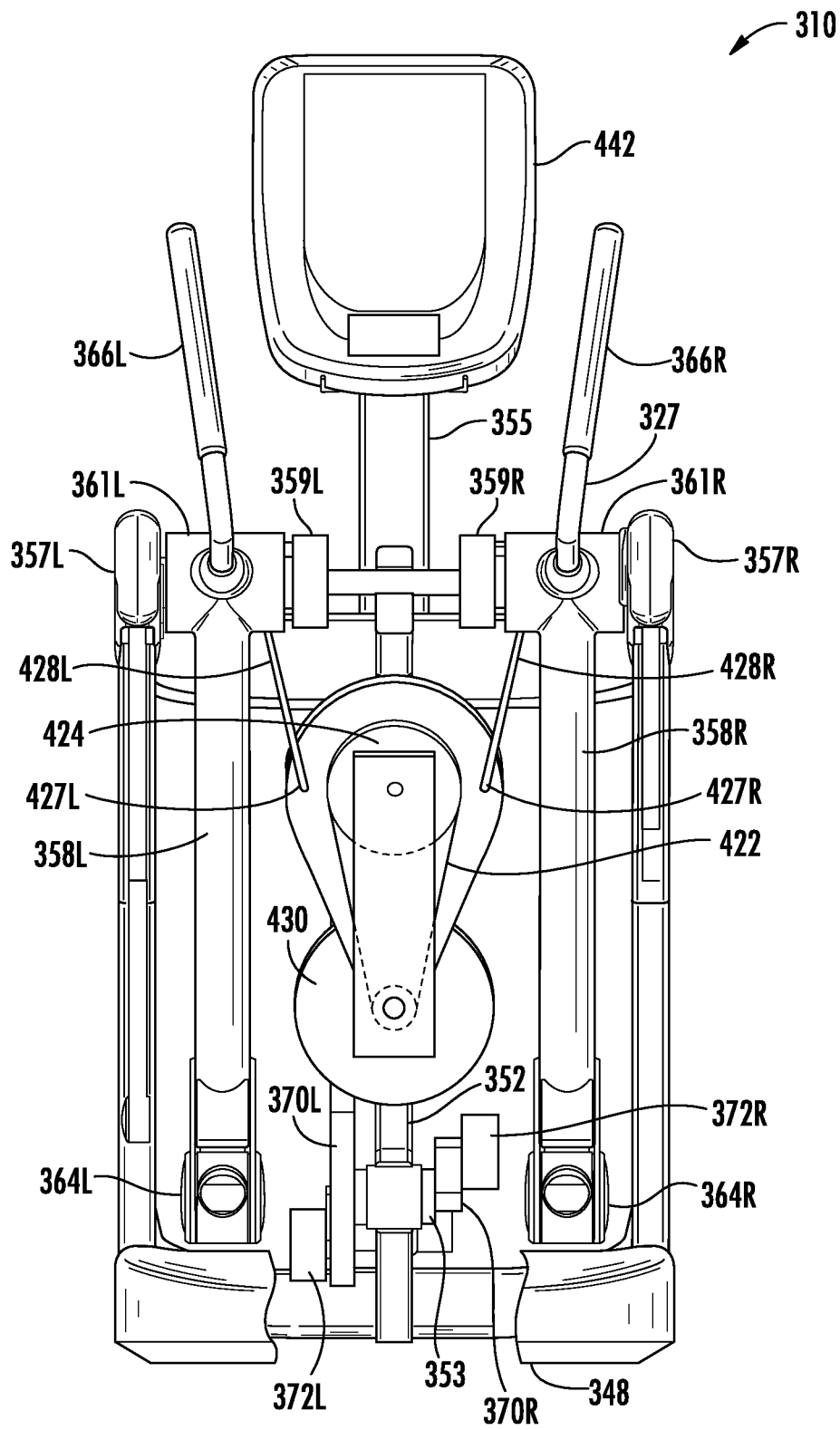
FIG. 14 is a rear elevational view of a portion of the exercise device of FIG. 8.

As shown by FIGS. 12-14, step height adjustment mechanism 338 comprises adjustment member 414 and actuator 416 connected by linkage 417. Step height adjustment mechanism 338 changes the location of front end flexible element mounts 398 which, in turn, modifies the paths of front flexible elements 406 and rear flexible elements 404 and adjusts the positions of foot pads 362.

Adjustment member 414 pivots vertically about a horizontal axis at the center of its attachment to frame 324. Front end flexible elements mounts 398 are located on the forward end of adjustment member 414. The rearward end of adjustment member 414 is connected to actuator 416 by linkage 417. As viewed from the left side of exercise apparatus 310, movement of linkage 417 downward pivots adjustment member 414 in a clockwise direction which increases the vertical position of front flexible element mounts 398. In the illustrated example, the pivot axis of adjustment member 414 is coincident with axis 374 of crank system 328. As a result, movement of front end flexible end mounts 398 from the lowest position to the highest position results in an increase in the overall step height or distance with a majority of the increase occurring at the upper end of the range of motion. In other words, the upper end or highest vertical height attained by the footpads 326 during their motion will rise by an extent nearly equaling the total increase in step height distance. The lowest point to which the footpads 326 fall in only minimally lowered. By way of example, it the step height or range is increased by a distance X, the highest vertical point of foot pads 326 may increase by a distance ⅘ X which the lowest vertical height will only fall by a distance ⅕ X. As a result, linkage assemblies 310 may be supported at a lower elevation with a reduced risk of the linkage assemblies 310 or their footpads 326 bottoming out as a result of step height adjustment.

In other embodiments, adjustment member 414 and crank system 328 may pivot or rotate about different axes. For example, the axis of adjustment member 414 and crank system 328 may be offset such that changes in the step height or step range (the distance between the highest and lowest points in the path of foot pads 326) are equally distributed such that an increase or decrease in step height or range will result in the highest vertical point and the lowest vertical point of the path of pads 326 being raised and lowered by substantially equal amounts. In yet other embodiments, the axis of adjustment member 414 and crank system 328 may be offset such that changes in the step height or step range are largely achieved at the lower end of the range of motion, the lowermost elevation changing by a much larger extent as compared to the extent to which the uppermost elevation of foot pads 326 changes.

Although front end flexible element mounts 398 are illustrated as moving in unison, front end flexible element mounts 398 may be supported so as to be movable independent of one another to different locations—either by being rotated or by being translated. In yet other embodiments, step height adjustment member may move linearly through a slotted or sliding mechanism or the like. Overall, the location of step height adjustment mechanism 338 on front post 352 with vertical movement of front end flexible element mounts 398 provides a more compact and efficient design.

Actuator 416 and linkage 417 comprise a mechanism configured to rotate or move the adjustment member 414 between a plurality of different positions so as to position and retain front end flexible element mounts 398 at different positions with respect to frame 324, cranks 369 and flexible element crank guides 372. In one embodiment, actuator 416 comprises a motor configured to rotationally drive a threaded shaft or screw threadably engaging a nut or internally threaded member connected to member 414. Rotation of the threaded shaft or screw results in member 414 being raised and lowered and pivoting about axis 374. In other embodiments, actuator 416 and linkage 417 may comprise other means for raising and lowering member 414. For example, actuator 416 may alternatively comprise a hydraulic or pneumatic piston and cylinder assembly. In yet another embodiment, after 416 may comprise an electric solenoid. In still other embodiments, actuator 416 may comprise various gears or cam arrangements.

Although actuator 417 is illustrated as being attached to frame 324 rearward of post—352 and being further attached to member 414 rearwardly of the pivot axis of member 414, in other embodiments, actuator 417 may alternatively be attached to the member 414 forwardly of the pivot axis of member 414, on the same side of the pivot axis as mounts 398. In yet other embodiment, actuator 417 may be supported on the forward side of front post 352 or on another part of frame 324.

Figure 15A:
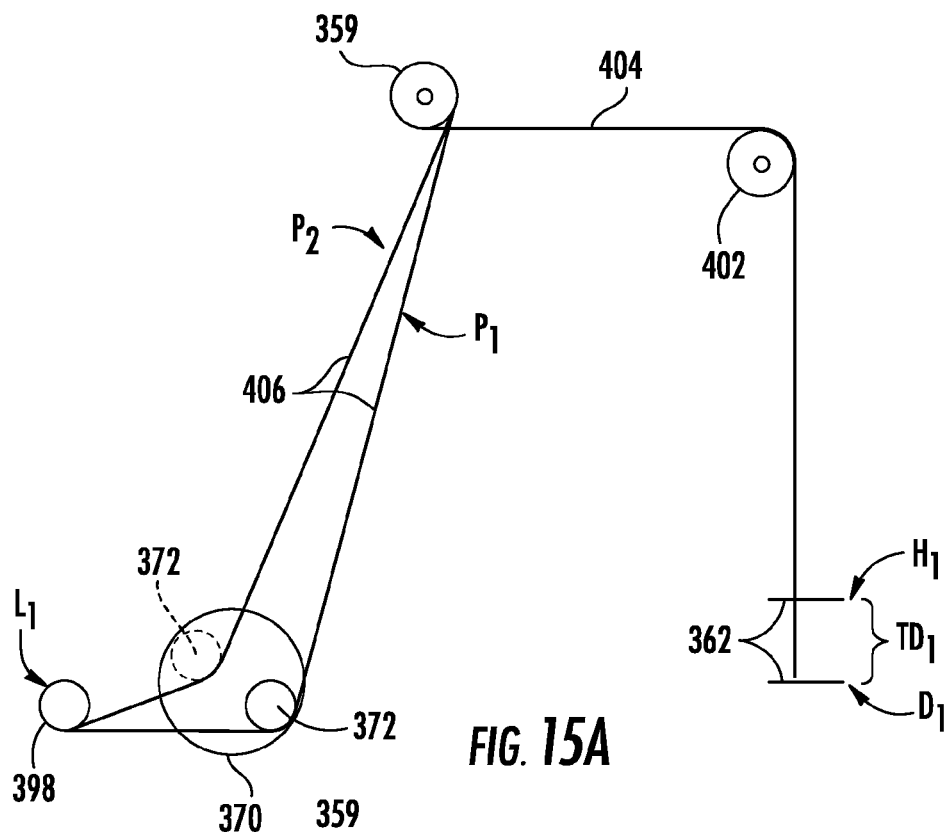
FIG. 15A is a diagram illustrating flexible elements of the exercise device of FIG. 8 at one step height setting.
Figure 15B:
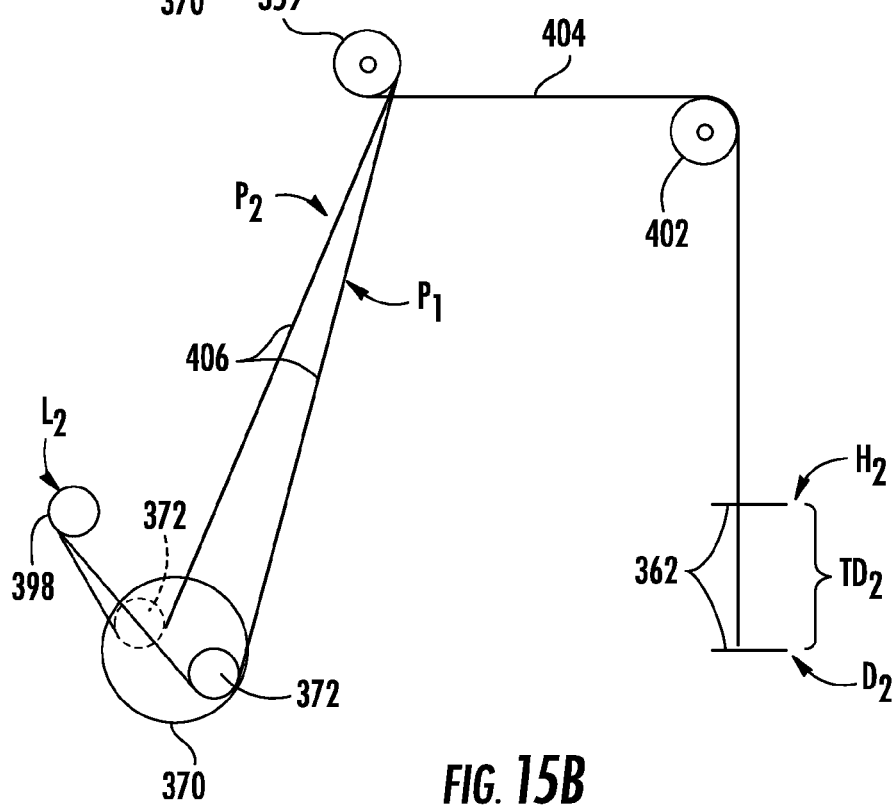
FIG. 15B is a diagram illustrating flexible elements of the exercise device of FIG. 8 at another step height setting.

FIGS. 15A and 15B diagrammatically illustrate the adjustment of travel distance achieved by the repositioning of front end flexible elements mounts 398. Both figures present an approximate elevation view of select components of step height adjustment mechanism 338, crank system 328, coupling system 334 and linkage assemblies 326. As shown by FIGS. 15A and 15B, repositioning front end flexible element mount 398 varies the amount or extent by which the front flexible element 406 wraps about the associated flexible element crank guide 372. This change in the amount of wrap changes the travel distance or travel range of foot supports 362. In one embodiment, the maximum step height, maximum step depth or both maximum step height and depth of the path through which footpads 362 may be adjusted.

FIG. 15A illustrates the approximate orientation of components when adjustment member 414 is pivoted to position front end flexible elements mounts 398 at their lowest point, L1. The resulting step height is "Low Travel Distance", TD1, which is the difference in the location of one of foot pads 362 at point H1 and the location of the other foot pad 362 at point D1. FIG. 15B illustrates the approximate orientation of components when adjustment member 414 is pivoted to position front end flexible elements mounts 398 at their highest point, L2. The resulting step height is "High Travel Distance", TD2, which is the difference in the location of one of foot pads 362 at point H2 and the location of the other foot pad 362 at point D2.

As illustrated by FIG. 15A, when front end flexible element mount 398 is at the lowest position L1, the combination of front flexible element 406 and rear flexible element 404 on one side of exercise apparatus 310 extends along path P1 resulting in foot pad 362 location at position H1. The combination of front flexible element 406 and rear flexible element 407 on the opposing side of exercise apparatus 310 extends along path P2 resulting in foot pad 362 at position D1. The distance between the first foot pad 362 position H1 and the second foot pad 362 position D1 is TD1, "Low Travel Distance". TD1 represents the minimum step height.

As illustrated by FIG. 15B, when front end flexible element mount 398 is at the highest position L2, the combination of front flexible element 406 and rear flexible element 404 on one side of exercise apparatus 310 extends through path P3 resulting in foot pad 362 position at H2. The combination of front flexible element 406 and rear flexible element 404 on the opposing side of exercise apparatus 310 extends along path P4 resulting in foot pad 362 position D2. The distance between the first foot pad 362 position H2 and the second foot pad 362 position D2 is TD2, "High Travel Distance". TD2 represents the maximum step height.

During pivoting of adjustment member 414, the amount of wrap of front flexible elements 406 around flexible element crank guides 372 changes. As the vertical location of front end flexible element mounts 398 rises from L1 toward L2, the amount of wrap increases which, in turn, changes the path of front flexible elements 406.

Each front flexible element 406 interfaces with a corresponding rear flexible element 404 at a torque bar 359. Front flexible element 406R wraps around and attaches to the torque bar inboard flexible element mount 401R. Rear flexible element 404R wraps around and attaches to torque bar outboard flexible element mount 400R. Rotation of the torque bars 359 around cross-shaft 349 translate movement between front flexible element 406 and rear flexible element 404. The total path length of each combination of front flexible element 406 and rear flexible element 404 remains essentially unchanged. A change in the position of the front flexible element mount 398 will result in a corresponding change to the position of foot pad flexible element mount 412, which repositions foot pads 362.

Increasing the wrap angle of front flexible element 406 around flexible element crank guide 372 increases the mechanical advantage of the user on the crank. Conversely, decreasing the wrap angle reduces the mechanical advantage of the user on the crank. By adjusting the position of front end flexible element mount 398, the maximum height and/or the maximum depth to which foot pad 362 may be raised or lowered may be adjusted. Likewise, the total range or total travel distance through which foot pad 362 is moved may also be adjusted Adjustment member 414 can be pivoted to a continuum of different positions and may be retained in any one position along the continuum. In other embodiments, adjustment member 414 may alternatively rotate between a multitude of distinct discrete spaced positions at various predetermined angles about its pivot point. In such an alternative embodiment, notches, detents or other retention mechanism may be used to define the distinct spaced positions at which adjustment member 414 may be retained.

Actuator 416 comprises a mechanism configured to move adjustment member 414. In the example illustrated, actuator 416 comprises a powered actuator driven by electrical power. In one embodiment, actuator 416 comprises an electric powered motor configured to drive a worm or lead screw arrangement to generate linear translation so as to rotate adjustment member 414 about axis 374. In yet another embodiment, actuator 416 may comprise an electric motor, such as a stepper motor, servomotor and the like, directly connected to a shaft secured to adjustment member 414 along axis 374 or connected to a shaft secured to adjustment member 414 by speed reducing device or gear train to selectively rotate adjustment member 414. In still other embodiments, actuator 416 may comprise electric solenoid or a hydraulic or a pneumatic piston-cylinder assembly operably coupled to adjustment member 414 so as to rotate adjustment member 414.

According to one embodiment, powered actuator 416 repositions adjustment member 414 to adjust the step height in response to control signals from a controller 446 associated with display 342. In one embodiment, such adjustment may be in response to a person depressing a button, sliding a slider bar, actuating a switch, entering a voice command to voice recognition software through microphone or other input. In another embodiment, such adjustment may be in accordance with a pre-programmed or predetermined exercise routine stored in memory, wherein the step height is to be adjusted during an exercise routine. Because such adjustment is powered and does not require a person to detach or disassemble any portion of exercise apparatus 310, such adjustment may be made "on-the-fly" during exercise as foot pads 362 are moving along a path. In other words, an exercise routine or workout need not be interrupted.

In other embodiments, actuator 416 may alternatively comprise a non-powered actuator. For example, actually 416 may alternatively be configured to be manually powered, wherein force or motion applied by a person is mechanically transmitted to adjustment member 414 to reposition adjustment member 414. After adjustment, adjustment member 414 may be retained in place by one or more hooks, clamps, catches, detents or friction surfaces.

Although adjustment member 414 is illustrated as being rotated so as to reposition end mounts 398 and so as to adjust the step height of exercise apparatus 310, in other embodiments, the positioning of end mounts 398 may be adjusted in other fashions. For example, in another embodiment, end mounts 398 may alternatively be linearly movable or configured to slide or translate between different positions relative to frame 324 and relative to crank flexible element guides 372.

Horizontal resistance system 340 comprises a system configured to apply additional resistance to or against horizontal movement of foot support members 360 and footpads 362. FIGS. 12-14 illustrate horizontal resistance system 340 in more detail. FIG. 14 is a rear view of exercise apparatus 310 with parts removed to reveal a rear view of horizontal resistance system 340. In the example illustrated, horizontal resistance system 340 is attached to the rearward side of front post 352 in an essentially vertical arrangement such that portions of resistance system 340 rotate about one or more horizontal axes. Such arrangement provides a more compact and efficient design of exercise apparatus 310. In other embodiments, resistance system 340 may be attached to a different side of front post 352 or to another portion of frame 324.

Horizontal resistance system 340 comprises connecting elements 428R, 428L (collectively referred to as connecting elements 428, upper element mounts 426R, 426L (collectively referred to as upper element mounts 426), lower element mounts 427R, 427L (collectively referred to as lower element mounts 427), resistance source 430 and rocker 424.

Connecting elements 428 comprise rigid linkages or rods. Each of connecting elements 428 has an upper end attached to one of upper element mounts 426 and a lower end attached to one of lower element mounts 427 eccentrically located on rocker 424. Element 428R is attached to mounts 426R and 427R. Element 428L is attached to mounts 426L and 427L. Upper element mounts 426 are attached to hubs 361 associated with linkage assemblies 326. Lower element mounts 427 are operably connected to rocker 424. In the example illustrated, mounts 426 and 427 comprise swivel, universal or pivot joints or the like. Linkage assemblies 326 rotate in opposite directions in response to the forces imposed by upon swing arms 327 and foot supports 360 by the person exercising. As one of linkage assemblies 326 rotates in a clockwise direction as viewed from the left side of exercise apparatus 310, the upper element mount 426 attached to that linkage assembly 326 correspondingly rotates. The rotation raises the vertical position of element mount 426 and creates upward force on and movement of the element 428 attached to the element mount 426. The upward movement of element 428 results in corresponding movement of lower element mount 427. The movement of lower element mount 427 creates movement of rocker 424, which is operably connected to resistance source 430. In other embodiments, mounts 426 may be secured to other portions of linkage assemblies 326.

Rocker 424 and belt 422 operably connect elements 428 to resistance source 430. Rocker 424 is rotationally driven upon movement of elements 428 against the resistance provided by resistance source 430.

Resistance source 430 comprises a mechanism configured to rotate against a selectively adjustable resistance. In one embodiment, resistance source 430 comprises a metal plate and one or more magnets forming an Eddy brake. In one embodiment, the one or more magnets comprise electromagnets, allowing the strength of the magnetic force to be selectively adjusted to control and vary the resistance applied against the rotation of hubs 361 of linkage assemblies 326. In another embodiment, resistance source 430 may comprise an electric generator. In still another embodiment, resistance source 430 may comprise two surfaces in frictional contact with one another so as to generate resistance against rotation of hubs 361. In another embodiment, air brakes may be utilized. In still other embodiments, other brakes or resistance mechanisms may be utilized. In one embodiment, the resistance applied by horizontal resistance source 430 may be selectively adjusted by a person using exercise apparatus 310. In one embodiment, the resistance may be adjusted in response to control signals generated by controller 446 associated with display 342 in response to input from a person exercising or in response to a stored exercise routine or workout. In still other embodiments, horizontal resistance system 340 may be omitted.

Display 342 comprises a mechanism facilitating interface between exercise apparatus 310 and a person exercising. As schematically showing FIG. 8, display 342 comprises inputs 440, outputs 442, communication interface 444 and controller 446 (each of which is schematically illustrated in FIG. 8). Inputs 140 comprise one or more mechanisms configured to facilitate entry of commands or information to exercise apparatus 310 from a person. In one embodiment, such inputs may comprise a touch screen, one or more push buttons, one or more slider bars, toggle switches, a microphone and voice recognition software and the like.

Outputs 442, corresponds to display 32 described above and comprises one or more devices configured to present information to a person. In one embodiment, outputs 442 may comprise a display screen, light emitting diodes, audible signal or sound generating devices and the like. Communication interface 444 comprises a mechanism facilitating communication between exercise apparatus 310 and external systems or devices such as a network, the Internet, or other exercise apparatus. Communication interface 444 may be configured to facilitate wired or wireless communication.

Controller 446 corresponds to controller 34 described above and comprises one or more processing units configured to receive information or commands from inputs 444 or communication interface 444 as well as information or data from various sensors associated with exercise apparatus 310. Controller 446 further analyzes such information and generate control signals directing the display of information by display 342, the transmission of data or information or information requests via communication interface 144 and the operation of resistance sources 392, and 430 as well as actuator 416. Controller 446 performs each of the function as noted above that are performed by controller 34. In particular, controller 446 cause output 442 to concurrently present visible tracings 36 forming a composite image or design 38. In one embodiment, controller 46 further presents a target shape 39 which outlined objective ranges of motion for footpads 326 as described above.

During use of exercise apparatus 310, a person mounts platform 348 while generally grasping side arms 356. While continuing to grasp side arms 356, a person then mounts foot pads 362. The person exercising then inputs via inputs 440 desired workout or exercise routine or selects a pre-stored workout or exercise routine. In response to such inputs, controller 446 may generate control signals adjusting the amount of resistance applied by resistance sources 392 and 430. In addition, controller 446 may generate control signals causing powered actuator 416 to reposition front end flexible element mounts 398 to adjust the step height. During the exercise routine, person exercising may decide to adjust his or her stride or the path of his or her stride. This is achieved by the person simply applying a different force to footpad 362 and linkage assemblies 326. In addition, the person exercising may decide to increase or decrease the step height. To do this, person may simply enter a change using input 440, wherein controller 446 generates control signals causing actuator 416 to reposition adjustment member 414 to adjust the step height. As noted above, this adjustment may be made on the fly during exercise. In other embodiments, controller 446 may automatically adjust the resistance applied by one or both of resistance sources 392 and 430 as well as the step height controlled by step height adjustment mechanism 338 in accordance with stored exercise routine or workout. Such changes may be made based upon the lapse of time from the beginning of the workout, based upon time remaining in the workout, based upon sensed biometrics of the person exercising or based upon predetermined speed, force or motion path objectives or targets being met or not being met. Because exercise apparatus 310 enables the maximum step height or maximum step depth to be automatically adjusted by controller 446 or to be adjusted by a person during exercise, exercise apparatus 310 provides more flexible or versatile exercise options and a more enjoyable workout.

Prior to initiating such exercise, person exercising may also provide commands to input 440 selecting a mode of operation wherein output 442 simultaneously or concurrently presents visible tracings 36 which are based at least in part upon paths completed by footpads 326. If so desired, the person may also choose or have chosen for him or her a target range of motions, represented by a target shape 39 (or other shape) to be completed. As a result, the person exercising is motivated to move footpads 36 through a diverse range of motions, enhancing the person strength and durability through a larger range of motions.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An exercise device comprising:
   a frame;
   a first member movably coupled to the frame so as to move with feet of a person;
   a display; and
   a controller configured to generate control signals causing the display to present a single continuous visible tracing that crosses itself and is based upon movement of the first member by the person during an exercise session, wherein the controller is configured to generate and display score for a workout, the score being based upon one or more factors selected from a group of factors consisting of: time to completely fill in an interior area of a target shape with the single continuous visible tracing; and accuracy-an extent to which the single continuous visible tracing extends outside of the interior area of the target shape.

2. The exercise device of claim 1, wherein the single continuous tracing changes color based upon an age of the single continuous visible tracing being displayed.

3. The exercise device of claim 1, wherein the single continuous visible tracing comprises different portions, each portion having a different color based upon a resistance level applied against movement of the first member.

4. The exercise device of claim 1, wherein the single continuous visible tracing comprises different portions, each portion having a different color, each different color being based upon and associated with a different resistance level applied against movement of the first member.

5. The exercise device of claim 1, wherein the single continuous visible tracing comprises different portions, each portion having a different color, each different color being based upon and associated with a different velocity of the first member.

6. The exercise device of claim 1, wherein the single continuous visible tracing has a line width based upon a duration of movement by the first member.

7. The exercise device of claim 1, wherein the single continuous visible tracing has different portions corresponding to different periods of time during which the first member moved, each portion having a different line width that is based upon and associated with a different resistance level applied against movement of the first member during the associated period of time.

8. The exercise device of claim 1, wherein the single continuous visible tracing comprises different portions, each portion having a different line width, each different line width being based upon and associated with a different velocity of the first member.

9. The exercise device of claim 1, wherein the single continuous visible tracing comprises different portions, each portion having a different graphic pattern, each different graphic pattern being based upon a characteristic of a path selected from a group of characteristics consisting of: resistance level against movement of the first member and repetitions.

10. The exercise device of claim 1, wherein the target shape to be filled comprises a target lobed shape having a first lobe, a second lobe and a third lobe defining an interior area for receiving the single continuous visible tracing, wherein the score is based upon one or more factors selected from a group of factors consisting of: time to completely fill in an interior area of the target lobed shape with the single continuous visible tracing; and accuracy-an extent to which the single continuous visible tracing extends outside of the interior area of the target lobed shape after the interior area of the target lobed shape has been completely filled.

11. The exercise device of claim 1, wherein the single continuous visible tracing overlaps itself at an intersection spaced from the interior boundaries of the target shape.

12. The exercise device of claim 1, wherein the first member is movably coupled to the frame so as to move with feet of a person through each of a plurality of different elliptical paths extending in a vertical plane and wherein the single continuous visible tracing is based upon movement of the first member by the person during an exercise session through each of the plurality of different elliptical paths extending in a vertical plane.

13. An exercise device comprising:
a frame;
a first member movably coupled to the frame so as to move with feet of a person;
a display; and
a controller configured to generate control signals causing the display to present a plurality of visible tracings, wherein the plurality of visible tracings is based upon movement of the first member by the person during an exercise session and wherein each of the plurality of tracings overlap one another; and
a user actuatable actuator configured to actuate between an active state and an inactive state, wherein, in the active state, visible tracings are added to existing already presented visible tracings that have been generated in response to movement of the first member during the exercise session and wherein, in the inactive state, visible tracings are not added despite movement of the first member.

14. The exercise device of claim 13 wherein the user actuatable actuator is depressable and is configured to execute or pause addition of visible tracings to existing already presented visible tracings only while being depressed.

15. The exercise device of claim 14, wherein actuation of the actuator executes the addition of visible tracings to existing already presented visible tracings that have been generated in response to force applied by the person to the first member during the exercise session, wherein prior to actuation, movement of the first member does not result in addition of visible tracings.

16. The exercise device of claim 14, wherein actuation of the actuator interrupts the addition of visible tracings to existing already presented visible tracings, despite ongoing movement of the first member and recording of data resulting from movement of the first member.

17. The exercise device of claim 13, wherein the plurality of visible tracings faun an image and wherein the controller is configured to store the image.

18. The exercise device of claim 13, wherein the controller is configured to automatically move a location of each of the plurality of visible tracing being generated.

19. The exercise device of claim 13, wherein the plurality of visible tracings cross at an intersection and wherein the controller is configured to generate control signals causing the display to present a target shape having interior boundaries defining an interior area for receiving and containing the intersection spaced from the interior boundaries.

20. The exercise device of claim 13, wherein the controller is configured to generate and display score for a workout, the score being based upon one or more factors selected from a group of factors consisting of: time to completely fill in the interior area of a target shape with the plurality of visible tracings; and accuracy-an extent to which the plurality of visible tracings extend outside of the interior area of the target shape.

* * * * *